(12) United States Patent
Plachetka

(10) Patent No.: US 9,345,695 B2
(45) Date of Patent: *May 24, 2016

(54) PHARMACEUTICAL COMPOSITIONS FOR THE COORDINATED DELIVERY OF NSAIDS

(71) Applicant: Pozen Inc., Chapel Hill, NC (US)

(72) Inventor: John R. Plachetka, Chapel Hill, NC (US)

(73) Assignee: Pozen Inc., Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/954,082

(22) Filed: Nov. 30, 2015

(65) Prior Publication Data

US 2016/0074376 A1 Mar. 17, 2016

Related U.S. Application Data

(60) Continuation of application No. 14/753,195, filed on Jun. 29, 2015, now Pat. No. 9,198,888, which is a continuation of application No. 14/515,627, filed on Oct. 16, 2014, now Pat. No. 9,161,920, which is a (Continued)

(51) Int. Cl.
*A61K 9/24* (2006.01)
*A61K 9/28* (2006.01)
*A61K 31/4439* (2006.01)
*A61K 31/192* (2006.01)

(52) U.S. Cl.
CPC .............. *A61K 31/4439* (2013.01); *A61K 9/209* (2013.01); *A61K 31/192* (2013.01)

(58) Field of Classification Search
None
See application file for complete search history.

(56) References Cited

U.S. PATENT DOCUMENTS

| | | |
|---|---|---|
| 4,198,390 A | 4/1980 | Rider |
| 4,255,431 A | 3/1981 | Junggren et al. |
| 4,344,929 A | 8/1982 | Bonsen et al. |
| 4,508,905 A | 4/1985 | Junggren et al. |
| 4,554,276 A | 11/1985 | LaMatina |

(Continued)

FOREIGN PATENT DOCUMENTS

| | | |
|---|---|---|
| AU | 2006235929 | 11/2006 |
| CA | 2139653 | 7/2001 |

(Continued)

OTHER PUBLICATIONS

"A 12 month, phase 3, open-label, multi-center study to evaluate the long—term safety of PN 400," *ClinicalTrials.gov*, Sep. 11, 2007, accessed from <http://clinicaltrials.gov/ct2/show/NCT00527904> on Sep. 6, 2012.

(Continued)

*Primary Examiner* — Nissa Westerberg
(74) *Attorney, Agent, or Firm* — Parker Highlander PLLC

(57) ABSTRACT

The present invention is directed to drug dosage forms that release an agent that raises the pH of a patient's gastrointestinal tract, followed by a non-steroidal anti-inflammatory drug. The dosage form is designed so that the NSAID is not released until the intragastric pH has been raised to a safe level. The invention also encompasses methods of treating patients by administering this coordinated release, gastroprotective, antiarthritic/analgesic combination unit dosage form to achieve pain and symptom relief with a reduced risk of developing gastrointestinal damage such as ulcers, erosions and hemorrhages.

4 Claims, 2 Drawing Sheets

Related U.S. Application Data continuation of application No. 14/231,971, filed on Apr. 1, 2014, now Pat. No. 8,865,190, which is a continuation of application No. 14/045,156, filed on Oct. 3, 2013, now Pat. No. 8,852,636, which is a continuation of application No. 13/215,855, filed on Aug. 23, 2011, now Pat. No. 8,557,285, which is a division of application No. 12/553,804, filed on Sep. 3, 2009, now abandoned, which is a division of application No. 11/129,320, filed on May 16, 2005, now Pat. No. 8,206,741, which is a continuation-in-part of application No. 10/158,216, filed on May 31, 2002, now Pat. No. 6,926,907.

(60) Provisional application No. 60/294,588, filed on Jun. 1, 2001.

(56) References Cited

U.S. PATENT DOCUMENTS

| | | |
|---|---|---|
| 4,562,261 A | 12/1985 | Hirata et al. |
| 4,619,934 A | 10/1986 | Sunshine et al. |
| 4,676,984 A | 6/1987 | Wu et al. |
| 4,704,278 A | 11/1987 | Wu et al. |
| 4,726,951 A | 2/1988 | Panoz et al. |
| 4,738,974 A | 4/1988 | Brandstrom |
| 4,757,060 A | 7/1988 | Lukacsko et al. |
| 4,758,579 A | 7/1988 | Kohl et al. |
| 4,766,117 A | 8/1988 | Crawford et al. |
| 4,786,505 A | 11/1988 | Lovgren et al. |
| 4,853,230 A | 8/1989 | Lovgren et al. |
| 4,865,847 A | 9/1989 | Gosswein |
| 4,948,581 A | 8/1990 | Sawayanagi et al. |
| 4,965,065 A | 10/1990 | Lukacsko et al. |
| 5,026,560 A | 6/1991 | Makino et al. |
| 5,035,899 A | 7/1991 | Saeki et al. |
| 5,037,815 A | 8/1991 | Lukacsko et al. |
| 5,043,358 A | 8/1991 | Lukacsko et al. |
| 5,051,262 A | 9/1991 | Panoz et al. |
| 5,093,132 A | 3/1992 | Makino et al. |
| 5,204,118 A | 4/1993 | Goldman et al. |
| 5,260,333 A | 11/1993 | Lukacsko et al. |
| 5,364,616 A | 11/1994 | Singer et al. |
| 5,373,022 A | 12/1994 | Fawzi et al. |
| 5,409,709 A | 4/1995 | Ozawa et al. |
| 5,417,980 A | 5/1995 | Goldman et al. |
| 5,466,436 A | 11/1995 | Stables |
| 5,514,663 A | 5/1996 | Mandel |
| 5,601,843 A | 2/1997 | Gimet et al. |
| 5,631,022 A | 5/1997 | Mandel et al. |
| 5,643,960 A | 7/1997 | Breitner et al. |
| 5,667,802 A | 9/1997 | Grimberg |
| 5,679,376 A | 10/1997 | Stevens et al. |
| 5,686,105 A | 11/1997 | Kelm et al. |
| 5,690,960 A | 11/1997 | Bengtsson et al. |
| 5,702,723 A | 12/1997 | Griffin |
| 5,714,504 A | 2/1998 | Lindberg et al. |
| 5,716,648 A | 2/1998 | Halskov et al. |
| 5,750,531 A | 5/1998 | Lee et al. |
| 5,817,338 A | 10/1998 | Bergstrand et al. |
| 5,817,340 A | 10/1998 | Roche et al. |
| 5,840,737 A | 11/1998 | Phillips |
| 5,872,145 A | 2/1999 | Plachetka |
| 5,877,192 A | 3/1999 | Lindberg et al. |
| 5,900,424 A | 5/1999 | Kallstrom et al. |
| 5,955,451 A | 9/1999 | Lichtenberger et al. |
| 6,013,281 A | 1/2000 | Lundberg et al. |
| 6,025,395 A | 2/2000 | Breitner et al. |
| 6,060,499 A | 5/2000 | Plachetka |
| 6,093,734 A | 7/2000 | Garst et al. |
| 6,132,768 A | 10/2000 | Sachs et al. |
| 6,132,771 A | 10/2000 | Depui et al. |
| 6,136,344 A | 10/2000 | Depui et al. |
| 6,160,020 A | 12/2000 | Ohannesian et al. |
| 6,162,816 A | 12/2000 | Bohlin et al. |
| 6,183,776 B1 | 2/2001 | Depui et al. |
| 6,183,779 B1 | 2/2001 | Ouali et al. |
| 6,207,188 B1 | 3/2001 | Gustavsson et al. |
| 6,231,888 B1 | 5/2001 | Lerner et al. |
| 6,287,600 B1 | 9/2001 | Ouali et al. |
| 6,365,184 B1 | 4/2002 | Depui et al. |
| 6,369,085 B1 | 4/2002 | Cotton et al. |
| 6,372,255 B1 | 4/2002 | Saslawski |
| 6,387,410 B1 | 5/2002 | Woolfe |
| 6,395,298 B1 | 5/2002 | Flannagan et al. |
| 6,428,810 B1 | 8/2002 | Bergstrand et al. |
| 6,485,747 B1 | 11/2002 | Flanagan et al. |
| 6,489,346 B1 | 12/2002 | Phillips |
| 6,544,556 B1 | 4/2003 | Chen et al. |
| 6,599,529 B1 | 7/2003 | Skinhoj et al. |
| 6,610,323 B1 | 8/2003 | Lundberg et al. |
| 6,613,354 B2 | 9/2003 | Depui et al. |
| 6,632,451 B2 | 10/2003 | Penhasi et al. |
| 6,641,838 B2 | 11/2003 | Pather et al. |
| 6,645,988 B2 | 11/2003 | Phillips |
| 6,673,819 B2 | 1/2004 | Bergman et al. |
| 6,685,964 B1 | 2/2004 | Bartholomaeus et al. |
| 6,699,885 B2 | 3/2004 | Phillips |
| 6,713,089 B1 | 3/2004 | Bertelsen et al. |
| 6,749,867 B2 | 6/2004 | Robinson et al. |
| 6,780,882 B2 | 8/2004 | Phillips |
| 6,787,164 B2 | 9/2004 | Gelber et al. |
| 6,797,283 B1 | 9/2004 | Edgren et al. |
| 6,869,615 B2 | 3/2005 | Chen et al. |
| 6,875,872 B1 | 4/2005 | Lindberg et al. |
| 6,926,907 B2 | 8/2005 | Plachetka |
| 7,029,701 B2 | 4/2006 | Chen |
| 7,030,162 B2 | 4/2006 | Plachetka et al. |
| 7,060,694 B2 | 6/2006 | Plachetka et al. |
| 7,094,425 B2 | 8/2006 | Scott et al. |
| 7,332,183 B2 | 2/2008 | Plachetka et al. |
| 7,399,772 B2 | 7/2008 | Phillips |
| 7,411,070 B2 | 8/2008 | Cotton et al. |
| 7,488,497 B2 | 2/2009 | Depui et al. |
| 7,745,466 B2 | 6/2010 | Cotton et al. |
| 7,785,626 B2 | 8/2010 | Pettersson et al. |
| 7,846,914 B2 | 12/2010 | Petrus |
| 8,206,741 B2 | 6/2012 | Plachetka et al. |
| 2001/0025107 A1 | 9/2001 | Barberich et al. |
| 2002/0012676 A1 | 1/2002 | Lundberg et al. |
| 2002/0042433 A1 | 4/2002 | Yelle et al. |
| 2002/0044962 A1 | 4/2002 | Cherukuri et al. |
| 2002/0045184 A1 | 4/2002 | Chen |
| 2002/0051814 A1 | 5/2002 | Chen |
| 2002/0086029 A1 | 7/2002 | Lundberg et al. |
| 2002/0090395 A1 | 7/2002 | Woolfe et al. |
| 2002/0111370 A1 | 8/2002 | Bergman et al. |
| 2002/0155153 A1 | 10/2002 | Depui et al. |
| 2002/0160046 A1 | 10/2002 | Robinson et al. |
| 2003/0008903 A1 | 1/2003 | Barberich et al. |
| 2003/0040537 A1 | 2/2003 | Plachetka et al. |
| 2003/0069255 A1 | 4/2003 | Plachetka |
| 2003/0113375 A1 | 6/2003 | Lundberg et al. |
| 2003/0129235 A1 | 7/2003 | Chen et al. |
| 2003/0215527 A1 | 11/2003 | Phillips |
| 2003/0232080 A1 | 12/2003 | Pather et al. |
| 2003/0232876 A1 | 12/2003 | Plachetka |
| 2004/0022846 A1 | 2/2004 | Depui et al. |
| 2004/0048896 A1 | 3/2004 | Phillips |
| 2004/0121004 A1 | 6/2004 | Taneja |
| 2004/0131676 A1 | 7/2004 | Taneja |
| 2004/0171646 A1 | 9/2004 | Phillips |
| 2004/0180089 A1 | 9/2004 | Plachetka et al. |
| 2005/0004171 A1 | 1/2005 | Phillips |
| 2005/0042304 A1 | 2/2005 | Phillips |
| 2005/0054682 A1 | 3/2005 | Phillips |
| 2005/0147668 A1 | 7/2005 | Bertelsen et al. |
| 2005/0163847 A1 | 7/2005 | Cheng et al. |
| 2005/0227949 A1 | 10/2005 | Edalatpour et al. |
| 2005/0249806 A1 | 11/2005 | Proehl et al. |
| 2005/0249811 A1 | 11/2005 | Plachetka |
| 2006/0165797 A1 | 7/2006 | Plachetka |
| 2006/0177504 A1 | 8/2006 | Sundharadas |

(56) References Cited

U.S. PATENT DOCUMENTS

| | | |
|---|---|---|
| 2006/0178348 A1 | 8/2006 | Plachetka |
| 2006/0178349 A1 | 8/2006 | Plachetka |
| 2006/0287284 A1 | 12/2006 | Schutze et al. |
| 2007/0122470 A1 | 5/2007 | Johansson et al. |
| 2007/0154542 A1 | 7/2007 | Tananbaum et al. |
| 2007/0184078 A1 | 8/2007 | Chen |
| 2007/0207200 A1 | 9/2007 | Plachetka et al. |
| 2007/0237820 A1 | 10/2007 | Cheng et al. |
| 2007/0243251 A1 | 10/2007 | Taneja |
| 2008/0031941 A1 | 2/2008 | Pettersson |
| 2008/0031950 A1 | 2/2008 | Sesha |
| 2008/0103169 A1 | 5/2008 | Phillips |
| 2009/0074863 A1 | 3/2009 | Taneja |
| 2009/0075950 A1 | 3/2009 | Taneja |
| 2009/0163551 A1 | 6/2009 | Earnest |
| 2009/0280173 A1 | 11/2009 | Chauhan et al. |
| 2009/0297594 A1 | 12/2009 | Depui et al. |
| 2010/0062064 A1 | 3/2010 | Ault et al. |
| 2010/0172983 A1 | 7/2010 | Plachetka |
| 2010/0178334 A1 | 7/2010 | Johansson et al. |
| 2010/0330179 A1 | 12/2010 | Ault et al. |
| 2012/0064156 A1 | 3/2012 | Plachetka |
| 2013/0078305 A1 | 3/2013 | Plachetka |

FOREIGN PATENT DOCUMENTS

| | | |
|---|---|---|
| DE | 40 35 455 | 5/1992 |
| DE | 198 01 811 | 1/1998 |
| EP | 0 005 129 | 10/1979 |
| EP | 0 124 495 | 11/1984 |
| EP | 0 166 287 | 1/1986 |
| EP | 0 167 958 | 1/1986 |
| EP | 0 174 726 | 3/1986 |
| EP | 0 244 380 | 11/1987 |
| EP | 0 320 550 | 6/1989 |
| EP | 0 320 551 | 6/1989 |
| EP | 0 426 479 A1 | 5/1991 |
| EP | 0 426 479 B1 | 5/1991 |
| EP | 0 550 083 | 7/1993 |
| EP | 1 020 461 | 7/2000 |
| EP | 1 068 867 | 1/2001 |
| EP | 1 726 300 | 11/2006 |
| EP | 1 726 301 | 11/2006 |
| EP | 1 411 900 | 7/2010 |
| GB | 2 105 193 | 3/1983 |
| GB | 2 163 747 | 3/1986 |
| GB | 2 216 413 | 10/1989 |
| JP | 2005-145894 | 6/2005 |
| WO | WO 85/03433 | 8/1985 |
| WO | WO 90/06925 | 6/1990 |
| WO | WO 91/16886 | 11/1991 |
| WO | WO 91/16895 | 11/1991 |
| WO | WO 91/16896 | 11/1991 |
| WO | WO 91/19711 | 12/1991 |
| WO | WO 91/19712 | 12/1991 |
| WO | WO 93/11750 | 6/1993 |
| WO | WO 93/12817 | 7/1993 |
| WO | WO 94/07541 | 4/1994 |
| WO | WO 94/27988 | 12/1994 |
| WO | WO 95/01977 | 1/1995 |
| WO | WO 95/32959 | 12/1995 |
| WO | WO 96/05177 | 2/1996 |
| WO | WO 96/05199 | 2/1996 |
| WO | WO 96/14839 | 5/1996 |
| WO | WO 96/22780 | 8/1996 |
| WO | WO 97/11701 | 4/1997 |
| WO | WO 97/25064 | 7/1997 |
| WO | WO 98/13073 | 4/1998 |
| WO | WO 98/22117 | 5/1998 |
| WO | WO 98/22118 | 5/1998 |
| WO | WO 98/54171 | 12/1998 |
| WO | WO 99/00380 | 1/1999 |
| WO | WO 99/12524 | 3/1999 |
| WO | WO 99/29320 | 6/1999 |
| WO | WO 99/66919 | 12/1999 |
| WO | WO 00/01368 | 1/2000 |
| WO | WO 00/15195 | 3/2000 |
| WO | WO 00/56339 | 9/2000 |
| WO | WO 00/71122 | 11/2000 |
| WO | WO 00/72838 | 12/2000 |
| WO | WO 00/78293 | 12/2000 |
| WO | WO 01/66088 | 3/2001 |
| WO | WO 01/24777 | 4/2001 |
| WO | WO 02/22108 | 3/2002 |
| WO | WO 02/066002 | 8/2002 |
| WO | WO 02/098352 | 12/2002 |
| WO | WO 03/017980 | 3/2003 |
| WO | WO 2004/062552 | 7/2004 |
| WO | WO 2004/064815 | 8/2004 |
| WO | WO 2005/074536 | 8/2005 |
| WO | WO 2005/074930 | 8/2005 |
| WO | WO 2006/044202 | 4/2006 |
| WO | WO 2007/064274 | 6/2007 |
| WO | WO 2007/078874 | 7/2007 |
| WO | WO 2008/101060 | 8/2008 |
| WO | WO 2009/012393 | 1/2009 |
| WO | WO 2009/145905 | 12/2009 |
| WO | WO 2010/151697 | 12/2010 |

OTHER PUBLICATIONS

"Astrazeneca AB, *Astrazeneca LP, KBI-E Inc., and Pozen, Inc.* v *Dr. Reddy's Laboratories Inc. and Dr. Reddy's Laboratories Ltd.*: Dr. Reddy's Laboratories Inc. and Dr. Reddy's Laboratories Ltd's. Invalidity contentions pursuant to L. Pat. R. 3.6(c)," dated Nov. 23, 2011.

"Astrazeneca AB, *Astrazeneca LP, KBI-E Inc., and Pozen, Inc.* V *Lupin Ltd. and Lupin Pharmaceuticals, Inc*.: Defendants Lupin Ltd. and Lupin Pharmaceuticals, Inc's Amended Invalidity Contentions Pursuant to L. PAT. R. 3.3 and 3.6(c)," dated Apr. 20, 2012.

"Astrazeneca AB, *Astrazeneca LP, KBI-E Inc., and Pozen, Inc.* v *Lupin Ltd. and Lupin Pharmaceuticals Inc*.,: Defendants Lupin Ltd. And Lupin Pharmaceuticals, Inc.'s Invalidity Contentions Pursuant to L. Pat. R. 3.3 and 3.6(c)," dated Nov. 23, 2011.

"Astrazeneca AB, *Astrazeneca LP, KBI-E Inc., and Pozen, Inc.* v. *Anchen Pharmaceuticals, Inc*.: Anchen's Initial Invalidity Contentions," dated May 11, 2012.

"Astrazeneca AB, *Astrazeneca LP, KBI-E Inc., and Pozen, Inc.* v. *Dr. Reddy's Laboratories Inc. and Dr. Reddy's Laboratories Ltd.*: Plaintiffs' Response to DRL's First Set of Interrogatories to Plaintiffs (Nos. 1-5)," dated Mar. 5, 2012.

"Histamine H2 antagonist," accessed from <drugs.com> on Sep. 6, 2012.

Notice of Paragraph IV Certification Re: Dr. Reddy's Laboratories, Ltd.'s and Dr. Reddy's Laboratories, Inc.'s Naproxen and Esomeprazole Magnesium Delayed Release Tablets; U.S. Pat. No. 6,926,907, from Dr. Reddy's Laboratories, Ltd./Dr. Reddy's Laboratories, Inc., dated Mar. 11, 2011.

"PK Study to evaluate esomeprazole plasma levels following the administration of PN 400," *ClinicalTrials.gov*, Jan. 11, 2008, accessed from <http://clinicaltrials.gov/ct2/show/NCT00599404> on Sep. 6, 2012.

"Study evaluating the bioavailability of Naproxen 500 mg in three formulations," *ClinicalTrials.gov*, Apr. 23, 2008, accessed from <http://clinicaltrials.gov/ct2/show/NCT00665743>, on Sep. 6, 2012.

Abelo et al., "Pharmacodynamic modeling of reversible gastric acid pump inhibition in dog and man," *European Journal of Pharmaceutical Sciences*, 14:339-346, 2001.

Alberts et al., "Efficacy and Safety of PA, a Novel Combination of Enteric-Coated Aspirin and Immediate-Release Omeprazole," *International Stroke Conference*, 2009, retrieved from the Internet at: http://www.pozen.com/wp-content/uploads/2011/08/ISC2009Albertsfile.pdf, retrieved Dec. 14, 2012.

Alexander et al., "Pilot evaluation of a novel combination table (PN 400) containing a proton pump inhibitor and a nonsteroidal antiinflammatory drug in prevention of upper gastrointestinal mucosal injury," *American Journal of Gastroenterology*, 100(9), S68, 135, 2005.

Andersson, "Pharmacokinetics, metabolism and interactions of acid pump inhibitors," *Clin. Pharmacokinet*., 31(1):9-28, 1996.

(56) References Cited

OTHER PUBLICATIONS

Anonymous, "Evaluate Relative Bioavailability of PA32540 (Asa/Omeprazole), Its Aspirin Component, and Ecotrin in Healthy Volunteers," ClinicalTrials.gov, Mar. 7, 2008, retrieved from the Internet at: http://www.clinicaltrials.gov/ct2/show/NCT00632086?term=aspirin+omeprazole&rank=18, retrieved on Dec. 28, 2012.
Anonymous, "POZEN' s PA32520 Study Data Demonstrated Better Upper Gastrointestinal Protection," Drugs.com, Nov. 11, 2008, retrieved from the Internet at: http://www.drugs.com/clinical_trials/pozen-s-pa32520-study-data-demonstrated-better-upper-gastrointestinal-protection-6195.html, retrieved Dec. 17, 2012.
Anonymous, "Study Evaluating the Effect of Gastroduodenal Muosa of PA32540, A32540 and Celecoxib, and Aspirin with Celecoxib (PA32540-109)," ClinicalTrials.gov, Jan. 9, 2009, retrieved from the Internet at: http://www.clinicaltrials.gov/ct2/show/NCT00700687?term=aspirin+omeprazole&rank=36, retrieved Dec. 18, 2012.
Anonymous, "Study to Evaluate the Incidence of Gastric Ulcers Following Administration of Either PA32540 or Enteric Coated Aspiring 325 mg in Subjects Who Are at Risk for Developing Aspirin-Associated Ulcers," ClinicalTrials.gov, Aug. 17, 2009, retrieved from the Internet at: http://clinicaltrials.gov/archive/NCT00960869/2009_08_17, retrieved Dec. 18, 2012.
Approval of Amendments/correction filed May 10, 2010 dated Jun. 21, 2010 (European application issued as EP 1 411 900 B1).
Awtry et al., "Aspirin," Circulation, 101:1206-1218, 2000.
Bajbouj et al., "A prospective multicenter clinical and endoscopic follow-up study of patients with gastroesophageal reflux disease," Z. Gastroenterol., 43:1303-1307, 2005.
Ballinger et al., "COX-2 inhibitors versus NSAIDs in gastrointestinal damage and prevention," Exp. Opin. Pharmacother., 2(1):31-40, 2001.
Barnett et al., "Effects of SCH 32651 on resting and stimulated acid secretion in guinea-pig isolated fundic mucosa," Br. J. Pharmac., 83:75-82, 1984.
Berardi et al,. "Elevation of gastric pH with rantidine does not affect the release characteristics of sustained release ibuprofen tablets," Biopharmaceutics & Drug Disposition, 9:337-347, 1998.
Bergmann et al., "Protection against aspirin-induced gastric lesions by lansoprazole: simultaneous evaluation of functional and morphologic responses," Clin. Pharmacol. Ther., 52:413-416, 1992.
Bianchi Porro et al., "Pantoprazole versus placebo in prevention of NSAID-induced ulcers," Gastroenterology, 114(4):A74, 1998.
Bianchi Porro et al., "Prevention of gastroduodenal damage with omeprazole in patients receiving continuous NSAIDs treatment. A double blind placebo controlled study," Ital. J. Gastroenterol. Hepatol., 30:43-47, 1998.
Bianchi Porro et al., "Why are non-steroidal anti-inflammatory drugs important in peptic ulcers?" Aliment. Pharmacol. Therap., 1:540S-547S, 1987.
Bigard et al., "Complete prevention by omeprazole of aspirin induced gastric lesions in healthy subjects," Gut, 29(5):A712, T49, 1988.
Bigard et al., "Effet protecteur de l'omeprazole sur les lesions gastriques induites par une prise unique d' aspirine chez l'homme," Gastroenterol. Clin. Biol., 12:770-771, 1998.
Bombardier et al., "Comparison of upper gastrointestinal toxicity of rofecoxib and naproxen in patients with rheumatoid arthritis," N. Engl. J. Med., 343:1520-1528, 2000.
Brown et al., "Aspirin- and indomethacin-induced ulcers and their antagonism by antihistamines," Euro. J. Pharm., 51:275-283, 1978.
Brown et al., "Prevention of the gastrointestinal adverse effects of nonsteroidal anti-inflammatory drugs," Pract. Drug Safety, 21:503-512, 1999.
Byrn et al., "Pharmaceutical solids: A strategic approach to regulatory considerations," Pharm. Res., 12(7): 945-954, 1995.
Carrasco-Portugal et al., "Bioavailability of a formulation containing a diclofenac-rantidine combination," Proc. West. Pharmacol. Soc., 45:8-10, 2002.

Chan et al., "Clopidogrel versus Aspirin and Esomeprazole to prevent recurrent ulcer bleeding," New Eng. J. Med., 352:238-244, 2005.
Chan et al., "Eradication of H. Pylori versus maintenance acid suppression to prevent recurrent ulcer hemorrhage in high risk NSAID users: A prospective randomized study," Gastroenterology, 114:A87, G0356, 1998.
Chandramouli et al., "Prevention and management of NSAID-Induced gastropathy," Journal of Pharmaceutical Pain and Symptom Control, 8(4):27-40, 2000.
Chang et al., "Polymetharcrylates," In: Handbook of Pharmaceutical Excipients, Fifth Edition, Ed. Raymond C. Rowe, Paul J. Sheskey and Sian C. Owen, London: Pharmaceutical Press, pp. 553-560, 2006.
Chen et al., "Esomeprazole tablet vs. omeprazole capsule in treating erosive esophagitis," World Journal of Gastroenterology, 11(20):3112-3117, 2005.
Cullen et al., "Primary gastroduodenal prophylaxis with omeprazole for non-steroidal anti-inflammatory drug users," Aliment. Pharmacol. Ther., 12:135-140, 1998.
Dajani, "Perspective on the gastric antisecretory effects of misoprostol in man," Prostaglandins, 33:68-77, 1987.
Daneshmend et al., "Abolition by omeprazole of aspirin induced gastric mucoasal injury in man," Gut, 31:514-517, 1990.
Daneshmend et al., "Use of microbleeding and an ultrathin endoscope to assess gastric mucosal protection by famotidine," Gastroenterology, 97:944-9, 1989.
Data sheet for "Arthrotec," 2009. (Document D8 from Letter to European Patent Office for counterpart European Application No. 02 734 602.2, regarding Oral Proceedings dated Dec. 18, 2009).
Dent, "Why proton pump inhibition should heal and protect against nonsteroidal anti-inflammatory drug users," Am. J. Med., 104:52S-55S, 1998.
Ehsanullah et al., "Prevention of gastroduodenal damage induced by non-steroidal anti-inflammatory drugs: controlled trial of ranitidine," BMJ, 297:1017-1021, 1998.
Ekstrom et al., Prevention of peptic ulcer and dyspeptic symptoms with omeprazole in pateitns receiving continuous non-steroidal anti-inflammatory drug therapy, Scand. J. Gastroenterol., 31:753-758, 1996.
Ene et al., "A study of the inhibitory effects of SCH 28080 on gastric secretion in man," Br. J. Pharmac., 76:389-391, 1982.
English translation of Bigard, et al., Gastroenterol. Clin. Biol., 12:770-771, 1998.
English translation of Muller et al, Arzneimittel Forschung, 47:758-760, 1997.
English translation of Muller et al., Arzneimittel-Forschung/Drug Res., 41(1):638-639, 1991.
English translation of Simon et al., Arzneimittel Forschung, 45:701-703, 1995.
Erlandsson et al., "Resolution of the enantiomers of omeprazole and some of its analogues by liquid chromatography on a trisphenycarbamoylcellulose-based stationary phase," J. Chromatog., 532:305-319, 1990.
European Search Report and Opinion issued in European application No. EP 09 17 8773, dated Feb. 11, 2010.
European Search Report issued in European application No. EP 02 734 602.2, dated May 29, 2007.
Extended European Search Report issued in European Patent Application No. 10792681.8, dated Jan. 4, 2013.
Fass, "Erosive Esophagitis and Nonerosive Reflux Disease (NERD): Comparison of Epidemiologic, Physiologic, and Therapeutic Characteristics," J. Clin. Gastroenterol., 41(2):131-137, 2007.
Feldman and Carlstedt, "Effect of antacid on absorption of enteric-coated aspirin," JAMA, 227(6):660-1, 1974.
Florence and Jani, "Novel oral drug formulations their potential in modulating adverse effects," Drug Safety, 10(3):233-66, 1994.
Fort et al., "Pa, a novel combination of delayed release (DR) aspirin (ASA) and immediate-release (IR) omeprazole, is associated with a decreased risk of gastroduodenal mucosal injury: Pooled data from three Phase I, 4-week endoscopic studies," American Journal of Gastroenterology, 103(Suppl. S):S487-S488, 2008.
Frank et al., "Reduction of indomerthacin induced gastrduodenal muclosal injury and gastrointestinal symptoms with cimetidine in normal subjects," J. Rheum., 16:1249-1252, 1989.

(56) References Cited

OTHER PUBLICATIONS

Gengo et al., "Prevalence of platelet nonresponsiveness to aspirin in patients treated for secondary stroke prophylaxis and in patients with recurrent isochemic events," *J. Clin. Pharmacol.*, 48:335-343, 2008.
Goldstein et al, "PN400 significantly reduces the incidence of gastric ulcers compared with enteric-coated naproxen in patients requiring chronic NSAID therapy regardless of low-dose aspirin use: Results from two phase 3 studies," POZEN Inc. sponsored study, 2009. (Document D16 from Letter to European Patent Office for counterpart European Application No. 02 734 602.2, regarding Oral Proceedings dated Dec. 18, 2009).
Goldstein et al., "116 A single table multilayer formulation of enteric-coated naproxen coupled with no-enteric-coated omeprazole is associated with a significantly reduced incidence of gastric ulcers vs. enteric-coated naproxen: A prospective, randomized double-blind study," 134(4), Supplement 1, A-19, 2008.
Goldstein et al., "PA32540 (Enteric-coated aspirin 325 mg + immediate-release omeprazole 40mg) is associated with significantly fewer gastric ulcers and significantly less endoscopic erosive esophagitis than enteric-coated aspirin (EC-ASA) alone: Results of two phase 3 studies," *The American Journal of Gastroenterology*, vol. 107, Suppl. 1, pp. S53-S54, 2012.
Goldstein et al., "PN400 significantly improves upper gastrointestinal tolerability compared with enteric-coated naproxen alone in patients requiring chronic NSAID therapy: Results from Two Prospective, Randomized, Controlled Trials," POZEN Inc. sponsored study, 2009. (Document D15 from Letter to European Patent Office for counterpart European Application No. 02 734 602.2, regarding Oral Proceedings dated Dec. 18, 2009).
Graham et al., "Duodenal and gastric ulcer prevention with misoprostol in arthritis pateitns taking NSAIDs," *Ann. Intern. Med.*, 119(4):257-262, 1993.
Grosser et al., "Thromboxane generation," In: Platelets, Alan Michelson Ed., pp. 565-574, Elseiver Science, 2007.
Gurbel et al., "Abstract 4267; PA32520 (Single-tablet of enteric-coated aspirin 325 mg + Immediate-release Omerpazole 20 mg); Aspirin therapy combining greater thrombozne suppression and lower upper gastrointestinal damage," *Circulation*, 118:S_855, 2008.
Gurbel et al., "PA32520 (Single-tablet of Immediate-Release Omeprazole 20 mg + Enteric-Coated Aspirin 325 mg): Safer Aspirin Therapy with Greater Thromboxane Suppression," Jul. 2009, retrieved from the Internet at: http://www.pozen.com/wp-content/themes/pozen/images/pdf/ISTH2009%20Pozen%20draft0701.pdf, retrieved Dec. 18, 2012.
Hart et al., "Aspirin dosage and thromboxane synthesis in patients with vascular disease," *Pharmacotherapy*, 23(5):579-584, 2003.
Hassan-Alin et al., "Lack of drug-drug interaction between esomeprazole and naproxen in healthy subjects," *Gastroenterology*, 124(4), Supp.1, A541, 2003.
Hawkey et al., "Omeprazole compared with misoprostol for ulcers associated with nonsteroidal anti-inflammatory drugs," *N. Eng. J. Med.*, 338:727-734, 1998.
Hawkey et al., "Prophylaxis of aspirin-induced gasf ric mucosal bleeding with ranitidine," *Aliment. Pharmacol. Therap.*, 2:245-252, 1988.
Hawkey et al., "Strategies for preventing aspirin-induced gastric bleeding," *Scandinavian Journal of Gastroenterology*, vol. 21, Supplement 125, pp. 170-173, 1986.
Hawkey, "Non-steroidal anti-inflammatory drug gastropathy: causes and treatment," *Scan. J. Gastroenterol.*, 31 Suppl. 220:124-7, 1996.
Hawkey, "Progress in prophylaxis against nonsteroidal anti-inflammatory drug-associated ulcers and erosions," *Am. J. Med.*, 104:67S-74S, 1998.
Hawkins et al., "The Gastroduodenal Toxicity of Nonsteroidal Anti-Inflammatory Drugs. A Review of the Literature," *J. Pain and Symptom Management*, 20(2):140-151, 2000.
Helander et al., "Structure and function of rat parietal cells during treatment with omeprazole, SCH 28080, SCH 32651, or ranitidine," *Scan. J. Gastroenterol.*, 25:799-809, 1990.

Hogan et al., "Prescription of nonsteroidal anti-inflammatory drugs for elderly people in Alberta," *Can. Med. Assoc.*, 151(3):315-322, 1994.
Howden, "Clinical pharmacology of omeprazole," *Clin. Pharmacokinet.*, 20:38-49, 1991.
Ife et al., "Reversible inhibitors of the Gastric $(H^+/K^+)$-ATpase. 3. 3-Substituted-4-(phenylamino)quinolines," *J med. Chem.*, 35:3413-3422, 1992.
Jacques et al., "Final purification, enrichment, of partially resolved enantiomer mixtures" In: Enantiomers, Racemates, and Resolutions, 423-434, 1981.
Jiranek et al., "Misoprostol reduces gastroduodenal injury from one week of aspirin: An endoscopic study," *Gastroenterology*, 96:656-661, 1989.
Johnson et al., "Esomeprazole once daily for 6 months is effective therapy for maintaining healed erosive esophagitis and for controlling gastroesophageal reflux disease symptoms: A randomized, double-blind, placebo-controlled study of efficacy and safety," *The American Journal of Gastroenterology*, 96(1):27-34, 2001.
Katz et al., "Gastric acidity and acid breakthrough with twice-daily omeprazole or iansoprazole," *Aliment. Pharmacol. Ther.*, 14:709-714, 2000.
Keeling et al., "SK&F 96067 is a reversible, lumenally acting inhibitor of the gastric $(H^+ + K^+)$-ATPase," *Biochemical Pharmacology*, 42(1):123-130, 1991.
Kephart et al., "Coprescribing of nonsteroidal anti-inflammatory drugs and cytoprotective and antiulcer drugs in Nova Scotia's senior populations," *Clin. Ther.*, 17:1159-1173, 1995.
Kimmey et al., "Role of $H_2$-receptor blockers in the prevention of gastric injury resulting from nonsteroidal anti-inflammatory agents," *Am. J. Med.*, 84:49-52, 1988.
Kitchingman et al., "Enhanced gastric mucosal bleeding with doses of aspirin used for prophylaxis and its reduction by rantidine," *Br. J Clin. Pharmac.*, 28:581-585, 1989.
Konturek et al., "Effects of omeprazole, a substituted benzimidazole, on gastrointestinal secretions, serum gastrin, and gastric mucosal blood flow in dogs," *Gastroenterology*, 86(1): 71-77, 1984.
Labenz et al., "Risk factors for erosive esophagitis: A multivariate analysis based on the proGERD study initiative," *American Journal of Gastroenterology*, 99:1652-1656, 2004.
Lad et al., "Management of nonsteroidal anti-inflammatory drug-induced gastroduodenal disease by acid suppression," *Can. J. Gastroenterol.*, 13:135-142, 1999.
Lanas, "Prevention of aspirin-induced gastroduodenal damage: H. Pylori infection eradication versus proton pump inhibitors or both," *Digestive and Liver Disease*, 36:655-657, 2004.
Lanza et al., "A double-blind placebo-controlled comparison of the efficacy and safety of 50, 100, and 200 µg of misoprostol QID in the prevention of ibuprofen-induced gastric and duodenal mucosal lesions and symptoms," *Am. J Gastroenterol.*, 84(6):633-636, 1989.
Lanza et al., "Double-blinded, placebo-controlled endoscopic comparison of the mucosal protective effects of misoprostol versus cimetidine on tolmetin-induced injury to the stomach and duodenum," *Gastroenterology*, 95:289-294, 1988.
Larsson et al., "Animal pharmadynamics of omeprazole. A survey of its pharmacological properties in vivo," *Scand J Gastroenterol Suppl.*, 108:23-35, 1985.
Lee et al., "Omeprazole prevents indomethacin-induced gastric ulcers in rabbits" *Aliment. Pharmacol. Ther.*, 10:571-576, 1996.
Leese et al., "Effects of celecoxib, a novel cyclooxygenase-2 inhibitor, on platelet function in healthy Adults: A randomized, controlled trial," *J. Clin. Pharmacol.*, 40:124-132, 2000.
Leonards and Levy, "Reduction or prevention of aspirin-induced occult gastrointestinal blood loss in man," *Clinical Pharmacology and Therapeutics*, 10(4):571-5, 1969.
Letter to European Patent Office for counterpart European Application No. 02 734 602.2, regarding Oral Proceedings dated Dec. 18, 2009.
Lichtenberger et al., "Nonsteroidal anti-inflammatory drug and phospholipid prodrugs: combination therapywith antisecretory agents in rats," *Gastroentereology*, 111:990-995, 1996.

(56) References Cited

OTHER PUBLICATIONS

Lin and Lu, "Role of pharmacokinetics and metabolism in drug discovery and development," *Pharmacological Reviews*, 49(4):403-449, 1997.
Maggi et al., "Press-coated tablets for the sequential pulsed administration of two different drugs," *Int. J. Pharm.*, 99:173-179, 1993.
Mason and Winer, "Kinetics of aspirin, salicylic acid, and salicyclic acid, and salicyluric acid following oral administration of aspirin as a tablet and two buffered solutions," *Journal of Pharmaceutical Sciences*, 70(3):262-5, 1981.
Mattsson et al., "Omeprazole provides protection against experimentally induced gastric mucosal lesions," *Eur. J. Pharmacol.*, 91:111-114, 1983.
McKeage et al., "Esomeprazole: a review of its use in the management of gastric acid-related diseases in adults," *Drugs*, 68(11):1571-1607, 2008.
Miner et al., "Clinical trial: evaluation of gastric acid suppression with three doses of immediate-release esomeprazole in the fixed-dose combination of PN 400 (naproxen/esomeprazole magnesium) compared with naproxen 500 mg and enteric-coated esomeprazole 20 mg: a randomized, open-label, Phase I study in healthy volunteers," *Aliment. Pharmacol. Ther.*, 32(3):414-424, 2010.
Miner et al., "PA32540, a tablet containing enteric-coated (EC) aspirin 325 mg and unbuffered immediate-release omeprazole 40 mg, provides percent time gastric pH >4 significantly less than EC omeprazole 40 mg, but with faster onset and less exposure to omeprazole," *Gastroenterology*, vol. 142, Issue 5, Supplement 1, p. S-3, 2012.
Miner et al., "T1969 Gastric acid suppression with PN400, a single-tablet, multilayer, fixed dose formulation combining an immediate-release esomeprazole layer and an enteric-coated (EC) naproxen core," *Gastroenterology*, 136(5), Suppl. 1, A-611, 2009.
Miner et al., "T1972 Pharmacokinetics of naproxen and esomeprazole in pn400, a single-tablet, multilayer formulation of enteric-coated naproxen coupled with immediate-release esomeprazole," *Gastroenterology*, 136(5), Suppl. 1, A-612, 2009.
Morgner et al., "Esomeprazole: prevention and treatment of NSAID-induced symptoms and ulcers," *Expert Opin Pharmacother.*, 8(7):975-988, 2007.
Morris et al., "Gastric cytoprotection is secondary to increased mucosal fluid secretion: A study of six cytoprotective agents in the rat," *J. Clin. Gastroenterol.*, 27(Suppl. 1):S53-63, 1998.
Morrison et al., "The optimal analgesic dose of rofecoxib: overview of six randomized controlled trials," *JADA*, 131:1729-1737, 2000.
Muller et al., "Untersuchungen zur schutzwirkung von lansoprazol auf die menschliche magenschleimhaut gegenuber niedrig dosierter acetylsalicylsaure," *Arzneimittel Forschung*, 47:758-760, 1997.
Muller et al., "Verbesserung der gastroduodenalen vertraglichkeit von azetylsalizylsaure durch ranitidine," *Arzneimittel-Forschung/Drug Res.*, 41(1):638-639, 1991.
Naesdal et al., "Gastro-duodenal protection in an era of cyclo-oxygenase-2-selective nonsteroidal anti-inflammatory drugs," *European Journal of Gastroenterology & Hepatology*, 13(12):1401-1406, 2001.
Nefesoglu et al., "Interaction of omeprazole with enteric-coated Salicylate tablets," *International Journal of Clinical Pharmacology and Therapeutics*, 36(10):549-553, 1998.
Neuvonen and Kivisto, "Enhancement of drug absorption by antacids," *Clin. Pharmacokinet.*, 27(2):120-8, 1994.
Notice of Allowance issued in U.S. Appl. No. 10/158,216, dated Mar. 29, 2005.
Notice of Allowance issued in U.S. Appl. No. 11/129,320, dated May 11, 2012.
Notice of Opposition to a European Patent, submitted against European Patent application No. EP 1 411 900 on Apr. 15, 2011.
Notice of Opposition to a European Patent, submitted against European Patent application No. EP 1 411 900 on Apr. 20, 2011.
Oddsson et al., "Comparison between ranitidine and omeprazole for protection against gastroduodenal damage caused by naproxen," *Scand. J. Gastroenterol.*, 27:1045-1048, 1992.
Oddsson et al., "Endoscopic findings in the stomach and duodenum after treatment with enteric-coated and plain naproxen tablets in healthy subjects," *Scand. J. Gastroenterol.*, 25:231-234, 1990.
Office Communication issued in Australian Patent Application No. 2010266026, dated Dec. 11, 2013.
Office Communication issued in Canadian Patent Application No. 2,449,098, dated Nov. 6, 2008.
Office Communication issued in Chinese Patent Application No. 201080037566.1, dated Jan. 10, 2014. (English translation of Chinese text).
Office Communication issued in Egyptian Patent Application No. 2121/2001, dated Apr. 13, 2013.
Office Communication issued in Eurasian Patent Application No. 201270071, dated Aug. 5, 2013. (English translation of Russian text).
Office Communication issued in European Patent Application 10 177 150.9, dated Nov. 4, 2010.
Office Communication issued in European Patent Application No. 02 734 602.2, dated Jun. 30, 2008.
Office Communication issued in European Patent Application No. 02 734 602.2, dated Dec. 18, 2007.
Office Communication issued in European Patent Application No. 02 734 602.2, dated Feb. 22, 2010.
Office Communication issued in European Patent Application No. 02 734 602.2, dated Apr. 29, 2010.
Office Communication issued in European Patent Application No. 10 177 150.9, dated Nov. 12, 2010.
Office Communication issued in Israeli Patent Application No. 159129, dated Aug. 22, 2010. (English translation).
Office Communication issued in Israeli Patent Application No. 159129, dated Feb. 16, 2010. (English translation).
Office Communication issued in Israeli Patent Application No. 159129, dated Jul. 7, 2009. (English translation).
Office Communication issued in Israeli Patent Application No. 159129, dated Aug. 8, 2007. (English translation).
Office Communication issued in Japanese Patent Application No. 2003-501394, dated Jul. 25, 2008. (English translation).
Office Communication issued in Japanese Patent Application No. 2003-501394, dated Jan. 5, 2010. (English translation).
Office Communication issued in Norwegian Patent Application No. 20035275, dated Jul. 14, 2011. (English Translation).
Office Communication issued in U.S. Appl. No. 10/158,216, dated Apr. 22, 2004.
Office Communication issued in U.S. Appl. No. 10/158,216, dated Oct. 20, 2004.
Office Communication issued in U.S. Appl. No. 13/215,855, dated Feb. 28, 2013.
Office Communication issued in U.S. Appl. No. 13/215,855, dated Jun. 6, 2012.
Office Communication issued in U.S. Appl. No. 11/129,320, dated Oct. 25, 2010.
Office Communication issued in U.S. Appl. No. 11/129,320, dated Nov. 19, 2009.
Office Communication issued in U.S. Appl. No. 11/129,320, dated Mar. 30, 2009.
Office Communication issued in U.S. Appl. No. 11/129,320, dated Sep. 22, 2008.
Office Communication issued in U.S. Appl. No. 11/129,320, dated Jun. 16, 2011.
Office Communication issued in U.S. Appl. No. 11/129,320, dated Jan. 17, 2012.
Office Communication issued in U.S. Appl. No. 12/823,082, dated Jul. 18, 2013.
Office Communication issued in U.S. Appl. No. 12/823,082, dated Sep. 17, 2012.
Office Communication issued in U.S. Appl. No. 11/129,320, dated Nov. 15, 2011.
Office Communication issued in U.S. Appl. No. 11/129,320, dated Mar. 7, 2012.
Office Communication issued in U.S. Appl. No. 11/129,320, dated Apr. 19, 2012.
Office Communication issued in U.S. Appl. No. 13/475,446, dated Mar. 11, 2013.

(56) References Cited

OTHER PUBLICATIONS

Office Communication issued in U.S. Appl. No. 12/822,612, dated Jul. 18, 2013.
Office Communication issued in U.S. Appl. No. 12/822,612, dated Sep. 14, 2012.
Office Communication issued in U.S. Appl. No. 13/215,855, dated Dec. 12, 2012.
Office Communication issued in U.S. Appl. No. 12/553,107, dated Jul. 30, 2012.
Office Communication issued in U.S. Appl. No. 12/553,107, dated Jan. 5, 2012.
Office Communication issued in U.S. Appl. No. 14/753,195, dated Aug. 14, 2015.
Okabe et al., "Antisecretory effect of leminoprazole on histamine-stimulated gastric acid secretion in dogs: potent local effect," *Jpn. J. Pharmacol.*, 69:91-100, 1995.
Okabe et al., "Pharmacological regulation of gastric acid secretion in the apical membrane of parietal cells; a new target for antisecretory drugs," *Journal of Physiology and Pharmacology*, 52(4):639-656, 2001.
Panara et al., "Effects of the novel anti-inflammatory compounds, N-[2-(cyclohexyloxy)-4-nitrophenyl] methanesulphonamide (NS-398) and 5-methanesulphonamido-6-(2,4-difluorothio-phenyl)-1-inda none (L-745,337), on the cyclo-oxygenase activity of human blood prostaglandin endoperoxide synthases," *British Journal of Pharmacology*, 116:2429-2434, 1995.
Pang et al., "Modeling of intestinal drug absorption: roles of transporters and metabolic enzymes (for the Gillette review series)" *Drug Metabolism and Disposition*, 31(12): 1507-1519, 2003.
Pasero et al., "Aceclofenac versus naproxen in the treatment of ankylosing spondylitis: A double-blind, controlled study," *Current Therapeutic Research*, 55(7):833-842, 1994.
Patrono et al., "Low-dose aspirin for the prevention of Atherothrombosis," *New Eng. J. Med.*, 353:2373-2383, 2005.
PCT International Preliminary Examination Report, issued in International Application No. PCT/US2002/017105, dated May 7, 2003.
PCT International Preliminary Report on Patentability issued in International Application No. PCT/US2009/003281, dated Nov. 30, 2010.
PCT International Preliminary Report on Patentability issued in International Patent Application No. PCT/GB2009/051108, dated Mar. 24, 2011.
PCT International Preliminary Report on Patentability issued in International Patent Application No. PCT/SE2010/050712, dated Jan. 4, 2012.
PCT International Search Report and Written Opinion issued in International Patent Application No. PCT/GB2009/051108, dated Nov. 13, 2009.
PCT International Search Report and Written Opinion issued in International Patent Application No. PCT/SE2010/050712, dated Sepember 20, 2010.
PCT International Search Report issued in International Application No. PCT/US02/17105, mailed Mar. 14, 2003.
PCT International Search Report issued in International Application No. PCT/US10/39864, dated Aug. 30, 2010.
PCT Supplemental International Search Report issued in International Patent Application No. PCT/GB2009/051108, dated Sepember 28, 2010.
PCT Supplementary International Search Report issued in International Patent Application No. PCT/SE2010/050712, dated Oct. 20, 2011.
PCT Written Opinion issued in International Application No. PCT/US10/39864, dated Aug. 30, 2010.
Petersen, "Doubts are raised on the safety of 2 popular arthritis drugs," *NY Times*, p. C1, Published May 22, 2001.
Pilbrant et al., "Development of an oral formulation of omeprazole," *Scand. J Gastroenterol.*, 20(Suppl. 109):113-120, 1985.
Pirmohamed et al., "Adverse drug reactions as cause of admission to hospital: prospective analysis of 18,820 patients," *Br. Med. J.*, 329:15-19, 2004.
Porter S.C., "Coating of Pharmaceutical Dosage Forms," in: A. Gennaro (Ed.), *Remington: the Science and Practice of Pharmacy*, 19th edition. 1650-1651, 1995.
Preliminary Amendment filed in U.S. Appl. No. 13/475,446, filed May 18, 2012.
Press Release for Vimovo, Oct. 16, 2009. (Document D14 from Letter to European Patent Office for counterpart European Application No. 02 734 602.2, regarding Oral Proceedings dated Dec. 18, 2009).
Qureshi et al., "Pharmacokinetics of two enteric-coated ketoprofen products in humans with or coadministration of omeprozole and comparison with dissolution findings," *Pharmaceutical Research*, 11(11):1669-1672, 1994.
Ramage et al., "Inhibition of food stimulated acid secretion by misoprostol, an orally active synthetic E1 analogue prostaglandin," *Br. J. Clin Pharmac.*, 19:9-12, 1985.
Raskin et al., "Misprostol dosage in the prevention of nonsteroidal anti-inflammatory drug-induced gastric and duodenal ulcers: a comparison of three regimens," *Ann. Intern. Med.*, 123(5):344-350, 1995.
*Remington's Pharmaceutical Sciences*, 17th ed., University of Sciences in Philadelphia, 1985.
Reply to EPO communication of Apr. 29, 2010, dated May 10, 2010 (German and French translation of claims omitted).
Richardson et al., "Proton pump inhibitors, pharmacology and rationale for use in gastrointestinal disorders," *Drugs*, 56(3):307-35, 1998.
Robinson et al., "Effects of ranitidine gastroduodenal mucosal damage induced by nonsteroidal anti-inflammatory drugs," *Dig. Disc. Sci.*, 34(3):424-428, 1989.
Roche Naproxen EC label, copyright 1999.
Roth et al., "Cimetidine therapy in nonsteroidal anti-inflammatory drug gastropathy: double-blind long-term evaluation," *Arch. Intern. Med.*, 147:1798-1801, 1987.
Rubinstein, "Gastrointestinal anatomy physiology and permeation pathways," *Enhancement in Drug Discovery*, CRC Press, 3-35, 2007.
Sangiah et al., "Effects of misoprostol and omeprazole on basal gastric pH and free acid content in horses," *Res. Vet. Sci.*, 47(3):350-354, 1989.
Savarino et al., "Effect of one-month treatment with nonsteroidal anti-inflammatory drugs (NSAIDs) on gastric pH of rheumatoid arthritis patients," *Digestive Diseases and Sciences*, 43:459-463, 1998.
Scarpignato et al., "Towards a GI safer anti-inflammatory therapy," *Gastroenterology International*, 186-215, 1999.
Scheiman et al., "Omeprazole ameliorates aspirin-induced gastroduonedal injury," *Digestive Diseases and Sciences*, 39(1):97-103, 1994.
Scheiman, "NSAID-induced peptic ulcer disease: a critical review of pathogenesis and management," *Dig. Dis.*, 12:210-222, 1994.
Scheiman, "Pathogensis of gastroduodenal injury due to nonsteroidal and anti-inflammatory drug: Implications for prevention and therapy," *Seminars in Arthritis and Rheumatism*, 21(4):259-268, 1992.
Scott and Sundell, "Inhibition of H+K+ ATPase by SCH 28080 and SCH 32651," *European Journal of Pharmacology*, 112:268-270, 1985.
Seitz et al., "Tablet Coating," In: The Theory and Practice of Industrial Pharmacy. Eds. Leon Lachman, Herbert A. Lieberman and Joseph L. Kanig. Philadelphia: Lea & Febiger, pp. 346-373, 1986.
Selway, "Potential hazards of long-term acid suppression," *Scand. J. Gastroenterol.*, 25(Suppl. 178):85-92, 1990.
Sharma et al., "Comparison of 24-hour intragastric pH using four liquid formulations of lansoprazole and omerprazole," *Am. J. Health-Syst. Pharm.*, 56(Suppl. 4):518-21, 1999.
Silverman, *The Organic Chemistry of Drug Design and Drug Action*, 2nd Edition, Academic Press, p. 102 & p. 527, 2004.
Silverstein et al., "Gastrointestinal toxicity with Celecoxib versus nonsteroidal anti-inflammatory drugs for osteoarthritis and rheumatoid arthritis; the CLASS study: A randomized controlled trial," *JAMA*, 284:1247-1255, 2000.
Silverstein et al., "Misoprostol reduces serious gastrointestinal complications in paetints with rheumatoid arthritis receiving nonsteroidal anti-inflammatory drugs," *Ann. Intern. Med.*, 123(4):241-249, 1995.

(56) References Cited

OTHER PUBLICATIONS

Simon et al., "Schutzwirkung von omeprazol genguber niedrig dosierter acetylsalicylsaure," *Arzneimittel Forschung*, 45:701-703, 1995.

Summons to Attend Oral Proceedings Pursuant to Rule 116(1): EPC, dated Sep. 3, 2009, issued in European Patent Application No. 02, 734 602.2.

Sung, "Management of nonsteroidal anti-inflammatory drug-related peptic ulcer bleeding," *Am. J. Med.*, 110(1A): 29S-32S, 2001.

Taha et al., "Famotidine for the prevention of peptic ulcers and oesophagitis in patients taking low-dose aspirin (FAMOUS): a phase III, randomized, double-blind, placebo-controlled trial," *Lancet*, 374:119-25, 2009.

Takeuchi et al., "Effects of topical application of acidified omeprazole on acid secretion and transmucosal potential difference in anesthetized rat stomachs," *Japan J. Pharmacol.*, 47:397-408, 1988.

Tronstad et al., "Gastroscopic findings after treatment with enteric-coated and plain naproxen tablets in healthy subjects," *Scand. J. Gastroenterol.*, 20:239-242, 1985.

Vane et al., "The future of NSAID therapy: selective COX-2 inhibitors," *IJCP*, 54(1):7-9, Jan./Feb. 2000.

von Unge et al., "Stereochemical assignment of the enantiomers of omeprazole from X-ray anaylysis of a fenchyloxymethyl derivative of (+)-(R)- omeprazole," *Tetrahedron*, 8(12):1967-1970, 1997.

Wagner et al., "Effects of nonsteroidal anti-inflammatory drugs on ulcerogensis and gastric secretion in pylorus-ligated rat," *Digestive Diseases and Sciences*, 40:134-140, 1995.

Wakitani et al., "Profile of JTE-522 as a human cyclooxygenase-2 inhibitor," *Jpn. J. Pharmacol.*, 78:365-371, 1998.

Wallmark et al., "The relationship between gastric acid secretion and gastric $H^+$, $K^+$-ATPase activity,"*J. Biol. Chem..*, 260(25): 13681-13684, 1985.

Warner et al., "Nonsteroidal drug selectives for cyclo-oxygenase-1 rather than cyclo-oxygenase-2 are associated with human gastrointestinal toxicity: a full in vitro analysis," *Proc. Natl. Acad. Sci. USA*, 96:7563-7568, 1999.

Weil et al, "Prophylactic aspirin and risk of peptic ulcer bleeding," *BMJ*, 310: 827-830, 1995.

Wilson et al., "Effects of misoprostol on gastric acid and mucus secretion in man," *Digestive Diseases and Sciences*, 31(2): 126S-129S, 1986.

Wolfe et al., "Acid suppression: optimizing therapy for gastroduodenal ulcer healing, gastroesophageal reflux disease, and stress related erosive syndrome," *Gastroenterology*, 18(2):59-531, 2000.

Wolfe et al., "Gastrointestinal toxicity of nonsteroidal anti-inflammatory drugs," *N. Engl. J. Med.*, 340:1888-1899, 1999.

Yeomans et al., "A comparison of omeprazole with rantidine for ulcers associated with nonsteroidal anti-inflammatory drugs," *N. Engl. J. Med.*, 338:719-726, 1998.

Yeomans et al., "Efficacy of esomeprazole (20 mg once daily) for reducing the risk of gastroduodenal ulcers associated with continuous use of low-dose aspirin," *American Journal of Gastroenterology*, 103:1-9, 2008.

Yeomans et al., "New data on healing of nonsteroidal anti-inflammatory drug-associated ulcers and erosions," *Am. J. Med.*, 104:56S-61S, 1998.

PHARMACEUTICAL COMPOSITIONS FOR THE COORDINATED DELIVERY OF NSAIDS

CROSS REFERENCE TO RELATED APPLICATIONS

The present application is a continuation of U.S. application Ser. No. 14/753,195, filed Jun. 29, 2015, issued as U.S. Pat. No. 9,198,888 on Dec. 1, 2015, which is a continuation of U.S. application Ser. No. 14/515,627, filed on Oct. 16, 2014, issued as U.S. Pat. No. 9,161,920 on Oct. 20, 2015, which is a continuation of U.S. application Ser. No. 14/231,971, filed on Apr. 1, 2014, issued as U.S. Pat. No. 8,865,190 on Oct. 21, 2014, which is a continuation of U.S. application Ser. No. 14/045,156, filed on Oct. 3, 2013, issued as U.S. Pat. No. 8,852,636 on Oct. 7, 2014, which is a continuation of U.S. application Ser. No. 13/215,855, filed on Aug. 23, 2011, issued as U.S. Pat. No. 8,557,285 on Oct. 15, 2013, which is a divisional of U.S. application Ser. No. 12/553,804 filed on Sep. 3, 2009, abandoned, which is a divisional of U.S. application Ser. No. 11/129,320 filed on May 16, 2005, issued as U.S. Pat. No. 8,206,741 on Jun. 26, 2012, which is a continuation-in-part of U.S. application Ser. No. 10/158,216, filed on May 31, 2002, issued as U.S. Pat. No. 6,926,907 on Aug. 9, 2005, which claims the benefit of U.S. provisional application No. 60/294,588, filed on Jun. 1, 2001. The entire contents of all applications are hereby incorporated by reference.

FIELD OF THE INVENTION

The present invention is directed to pharmaceutical compositions that provide for the coordinated release of an acid inhibitor and a non-steroidal anti-inflammatory drug (NSAID). These compositions; have a reduced likelihood of causing unwanted side effects, especially gastrointestinal side effects, when administered as a treatment for pain, arthritis and other conditions amenable to treatment with NSAIDs.

BACKGROUND OF THE INVENTION

Although non-steroidal anti-inflammatory drugs are widely accepted as effective agents for controlling pain, their administration can lead to the development of gastroduodenal lesions, e.g., ulcers and erosions, in susceptible individuals. It appears that a major factor contributing to the development of these lesions is the presence of acid in the stomach and upper small intestine of patients. This view is supported by clinical studies demonstrating an improvement in NSAID tolerability when patients are also taking independent doses of acid inhibitors (*Dig. Dis.* 12:210-222 (1994); *Drug Safety* 21:503-512 (1999); *Aliment. Pharmacol. Ther.* 12:135-140 (1998); *Am. J. Med.* 104(3A):67S-74S (1998); *Clin. Ther.* 17:1159-1173 (1995)). Other major factors contributing to NSAID-associated gastropathy include a local toxic effect of NSAIDs and inhibition of protective prostaglandins (*Can. J. Gastroenterol.* 13:135-142 (1999) and *Pract. Drug Safety* 21:503-512, (1999)), which may also make some patients more susceptible to the ulcerogenic effects of other noxious stimuli.

In general, more potent and longer lasting acid inhibitors, such as proton pump inhibitors, are thought to be more protective during chronic administration of NSAIDs than shorter acting agents, e.g., histamine $H_2$ receptor antagonists (H-2 blockers) (*N. Eng. J. Med.* 338:719-726 (1998); *Am. J. Med.* 104(3A):56S-61S (1998)). The most likely explanation for this is that gastric pH fluctuates widely throughout the dosing interval with short acting acid inhibitors leaving the mucosa vulnerable for significant periods of time. In particular, the pH is at its lowest point, and hence the mucosa is most vulnerable, at the end of the dosing interval (least amount of acid inhibition) and for some time after the subsequent dose of acid inhibitor. In general, it appears that when a short acting acid inhibitor and an NSAID are administered simultaneously, NSAID-related mucosal damage occurs before the pH of the gastrointestinal tract can be raised and after the acid inhibiting effect of the short acting acid inhibitor dissipates.

Although longer lasting agents, such as proton pump inhibitors (PPIs), usually maintain a consistently higher gastroduodenal pH throughout the day, their antisecretory effect may be delayed for several hours and may not take full effect for several days (*Clin. Pharmacokinet.* 20:38-49 (1991)). Their effect may be diminished toward the end of the usual dosing interval. Intragastric pH rises particularly slowly with the first dose in a course of treatment since this class of drugs is enteric coated to avoid destruction by stomach acid. As a result, absorption is delayed for several hours. Even then, some patients fail to respond consistently to drugs of this type and suffer from "acid breakthrough" which again leaves them vulnerable to NSAID-associated gastroduodenal damage (*Aliment. Pharmacol. Ther.* 14:709-714 (2000)). Despite a significant reduction in gastroduodenal lesions with the concomitant administration of a proton pump inhibitor during six months of NSAID therapy, up to 16% of patients still develop ulcers, indicating that there remains substantial room for improvement (*N. Eng. J. Med.* 338:727-734 (1998)). Thus, the addition of a pH sensitive enteric coating to an NSAID could provide additional protection against gastroduodenal damage not provided by the H2 blocker or PPI alone. In addition, although long acting acid inhibitors may reduce the risk of GI lesions in chronic NSAID users, there are questions about the safety of maintaining an abnormally elevated pH in a patient's GI tract for a prolonged period of time (*Scand. J. Gastroenterol. Suppl.* 178:85-92 (1990)).

Recognizing the potential benefits of PPIs for the prevention of NSAID-induced gastroduodenal damage, others have disclosed strategies for combining the two active agents for therapeutic purposes. However, these suggestions do not provide for coordinated drug release or for reducing intragastric acid levels to a non-toxic level prior to the release of NSAID (U.S. Pat. Nos. 5,204,118; 5,417,980; 5,466,436; and 5,037,815). In certain cases, suggested means of delivery would expose the gastrointestinal tract to NSAIDs prior to onset of PPI activity (U.S. Pat. No. 6,365,184).

Attempts to develop NSAIDs that are inherently less toxic to the gastrointestinal tract have met with only limited success. For example, the recently developed cyclooxygenase-2 (COX-2) inhibitors show a reduced tendency to produce gastrointestinal ulcers and erosions, but a significant risk is still present, especially if the patient is exposed to other ulcerogens (*JAMA* 284:1247-1255 (2000); *N. Eng. J. Med.* 343:1520-1528 (2000)). In this regard, it appears that even low doses of aspirin will negate most of the benefit relating to lower gastrointestinal lesions. In addition, the COX-2 inhibitors may not be as effective as other NSAIDs at relieving some types of pain and have been associated with significant cardiovascular problems (*JADA* 131:1729-1737 (2000); *SCRIP* 2617, pg. 19, Feb. 14, 2001); NY Times, May 22, 2001, pg. C1)).

Other attempts to produce an NSAID therapy with less gastrointestinal toxicity have involved the concomitant administration of a cytoprotective agent. In 1998, Searle began marketing Arthrotec™ for the treatment of arthritis in patients at risk for developing GI ulcers. This product contains misoprostol (a cytoprotective prostaglandin) and the NSAID diclofenac. Although patients administered Arthrotec™ do have a lower risk of developing ulcers, they may experience a number of other serious side effects such as diarrhea, severe cramping and, in the case of pregnant women, potential damage to the fetus.

Another approach has been to produce enteric coated NSAID products. However, even though these have shown modest reductions in gastroduodenal damage in short term studies (*Scand. J. Gastroenterol.* 20: 239-242 (1985) and *Scand. J. Gastroenterol.* 25:231-234 (1990)), there is no consistent evidence of a long term benefit during chronic treatment.

Overall, it may be concluded that the risk of inducing GI ulcers is a recognized problem associated with the administration of NSAIDs and that, despite considerable effort, an ideal solution has not yet been found.

SUMMARY OF THE INVENTION

The present invention is based upon the discovery of a new method for reducing the risk of gastrointestinal side effects in people taking NSAIDs for pain relief and for other conditions, particularly during chronic treatment. The method involves the administration of a single, coordinated, unit-dose product that combines: a) an agent that actively raises intragastric pH to levels associated with less risk of NSAID-induced ulcers; and b) an NSAID that is specially formulated to be released in a coordinated way that minimizes the adverse effects of the NSAID on the gastroduodenal mucosa. Either short or long acting acid inhibitors can be effectively used in the dosage forms. This method has the added benefit of being able to protect patients from other gastrointestinal ulcerogens whose effect may otherwise be enhanced by the disruption of gastroprotective prostaglandins due to NSAID therapy.

In its first aspect, the invention is directed to a pharmaceutical composition in unit dosage form suitable for oral administration to a patient. The composition contains an acid inhibitor present in an amount effective to raise the gastric pH of a patient to at least 3.5, preferably to at least 4, and more preferably to at least 5, when one or more unit dosage forms are administered. The gastric pH should not exceed 7.5 and preferably should not exceed 7.0. The term "acid inhibitor" refers to agents that inhibit gastric acid secretion and increase gastric pH. In contrast to art teaching against the use of H2 blockers for the prevention of NSAID-associated ulcers (*N. Eng. J. Med.* 340:1888-1899 (1999)), these agents are preferred compounds in the current invention. Specific H2 blockers that may be used include cimetidine, ranitidine, ebrotidine, pabutidine, lafutidine, loxtidine or famotidine. The most preferred acid inhibitor is famotidine present in dosage forms in an amount of between 5 mg and 100 mg.

Other preferred agents that may be effectively used as acid inhibitors are the proton pump inhibitors such as omeprazole, esomeprazole, pantoprazole, lansoprazole, rabeprazole, pariprazole, leminoprazole and tenatoprazole. Examples of particular proton pump inhibitors include omeprazole, present in unit dosage forms in an amount of between 5 mg and 50 mg; lansoprazole, present in unit dosage forms in an amount of between 5 mg and 150 mg (and preferably at between 5 mg and 30 mg); and pantoprazole, present in unit dosage forms in an amount of between 10 mg and 200 mg. Recently, a newer class of acid inhibitor has been developed which competes with potassium at the acid pump. The compounds in this class have been referred to as "reversible proton pump inhibitors" or "acid pump antagonists" and may also be used in the present invention. Examples include AZD-0865, AR-H047108, CS-526, pumaprazole, revaprazan and soraprazan (see WO9605177 and WO9605199). Other compounds in this group are H-335/25 (AstraZeneca, Dialog file 128, accession number 020806); Sch-28080 (Schering Plough, Dialog file 128, accession number 009663); Sch-32651 (Schering Plough, Dialog file 128, accession number 006883) and SK&F-96067 (CAS Registry no. 115607-61-9).

The pharmaceutical composition also contains a non-steroidal anti-inflammatory drug in an amount effective to reduce or eliminate pain or inflammation. The NSAID may be celecoxib, rofecoxib, lumiracoxib, valdecoxib, parecoxib, etoricoxib, CS-502, JTE-522, L-745,337, NS398, aspirin, acetaminophen (considered to be an NSAID for the purposes of the present invention), ibuprofen, flurbiprofen, ketoprofen, naproxen, oxaprozin, etodolac, indomethacin, ketorolac, lornoxicam, meloxicam, piroxicam, droxicam, tenoxicam, nabumetone, diclofenac, meclofenamate, mefenamic acid, diflunisal, sulindac, tolmetin, fenoprofen, suprofen, benoxaprofen, aceclofenac, tolfenamic acid, oxyphenbutazone, azapropazone, and phenylbutazone. The most preferred NSAID is naproxen in an amount of between 50 mg and 1500 mg, and more preferably, in an amount of between 200 mg and 600 mg. It will be understood that, for the purposes of the present invention, reference to an acid inhibitor, NSAID, or analgesic agent will include all of the common forms of these compounds and, in particular, their pharmaceutically acceptable salts. The amounts of NSAIDs which are therapeutically effective may be lower in the current invention than otherwise found in practice due to potential positive kinetic interaction and NSAID absorption in the presence of an acid inhibitor.

Preferably, the pharmaceutical composition of the present invention is in the form of a tablet or capsule that has: (a) the acid inhibitor present in an amount effective to raise the gastric pH of a patient to at least 3.5 upon the administration of one or more unit dosage forms; and (b) the non-steroidal anti-inflammatory drug (NSAID) present in an amount effective to reduce or eliminate pain or inflammation in a patient upon administration of one or more of said unit dosage forms. The NSAID in the dosage form should be in a core, preferably a single core when tablets are used, that is surrounded by a coating that does not release NSAID until the pH of the surrounding medium is 3.5 or higher. In the case of capsules, there may be several cores of NSAID, i.e., there may be multiple particles, each being surrounded by a coating that does not release NSAID until the pH of the surrounding medium is 3.5 or higher. The acid inhibitor is in one or more layers outside of the core which do not contain any NSAID. These layers are not surrounded by an enteric coating and, upon ingestion of the tablet or capsule by a patient, release the acid inhibitor into the patient's stomach.

The term "unit dosage form" as used herein refers to a single entity for drug administration. For example, a single tablet or capsule combining both an acid inhibitor and an NSAID would be a unit dosage form. A unit dosage form of the present invention preferably provides for coordinated drug release in a way that elevates gastric pH and reduces the deleterious effects of the NSAID on the gastroduodenal mucosa, i.e., the acid inhibitor is released first and the release of NSAID is delayed until after the pH in the GI tract has risen.

In a preferred embodiment, the unit dosage form is a multilayer tablet, having an outer layer comprising the acid inhibitor and an inner core which comprises the NSAID. In the most preferred form, coordinated delivery is accomplished by having the inner core surrounded by a polymeric barrier coating that does not dissolve unless the surrounding medium is at a pH of at least 3.5, preferably at least 4 and more preferably, at least 5. Alternatively, a barrier coating may be employed which controls the release of NSAID by time, as opposed to pH, with the rate adjusted so that NSAID is not released until after the pH of the gastrointestinal tract has risen to at least 3.5, preferably at least 4, and more preferably at least 5. Thus, a time-release formulation may be used to prevent the gastric presence of NSAID until mucosal tissue is no longer exposed to the damage enhancing effect of very low pH.

One NSAID of special interest in dosage forms is aspirin which not only provides relief from pain and inflammation but may also be used in low doses by patients to reduce the risk of stroke, heart attack and other conditions. Thus, pharmaceutical compositions may contain an acid inhibitor in combination with aspirin in an amount effective, upon the administration of one or more unit dosage forms, to achieve any of these objectives. As with the compositions described above the unit dosage form can be a tablet or capsule in which aspirin is present in a core and is surrounded by a coating that does not release the aspirin until the pH of the surrounding medium is 3.5 or higher. The acid inhibitor is in one or more layers outside the core, which do not include an NSAID, are not surrounded by an enteric coating; and, upon ingestion of the dosage form by a patient, release the acid inhibitor into the patient's stomach. Any of the acid inhibitors described herein may be used in the aspirin-containing dosage forms. In dosage forms designed for providing low dose aspirin therapy to patients, the aspirin should typically be present at 20-200 mg.

The invention includes methods of treating a patient for pain, inflammation and/or other conditions by administering the pharmaceutical compositions described above. Although the method may be used for any condition in which an NSAID is effective, it is expected that it will be particularly useful in patients with osteoarthritis or rheumatoid arthritis. Other conditions that may be treated include, but are not limited to: all forms of headache, including migraine headache; acute musculoskeletal pain; ankylosing spondylitis; dysmenorrhoea; myalgias; and neuralgias.

In a more general sense, the invention includes methods of treating pain, inflammation and/or other conditions by orally administering an acid inhibitor at a dose effective to raise a patient's gastric pH to at least 3.5, preferably to at least 4 or and more preferably to at least 5. The patient is also administered an NSAID, for example in a coordinated dosage form, that has been coated in a polymer that only dissolves at a pH of at least 3.5, preferably at least 4 and, more preferably, 5 or greater or which dissolves at a rate that is slow enough to prevent NSAID release until after the pH has been raised. When acid inhibitor and NSAID are administered in separate doses, e.g., in two separate tablets, they should be given concomitantly (i.e., so that their biological effects overlap) and may be given concurrently, i.e., NSAID is given within one hour after the acid inhibitor. Preferably, the acid inhibitor is an H2 blocker and, in the most preferred embodiment, it is famotidine at a dosage of between 5 mg and 100 mg. Proton pump inhibitors may also be used and offer advantages in terms of duration of action. Any of the NSAIDs described above may be used in the method but naproxen at a dosage of between 200 and 600 mg is most preferred. It is expected that the acid inhibitor and analgesic will be typically delivered as part of a single unit dosage form which provides for the coordinated release of therapeutic agents. The most preferred dosage form is a multilayer tablet having an outer layer comprising an H2 blocker or a proton pump inhibitor and an inner core comprising an NSAID.

The invention also provides a method for increasing compliance in a patient requiring frequent daily dosing of NSAIDs by providing both an acid inhibitor and NSAID in a single convenient, preferably coordinated, unit dosage form, thereby reducing the number of individual doses to be administered during any given period.

DETAILED DESCRIPTION OF THE INVENTION

Figure 1:
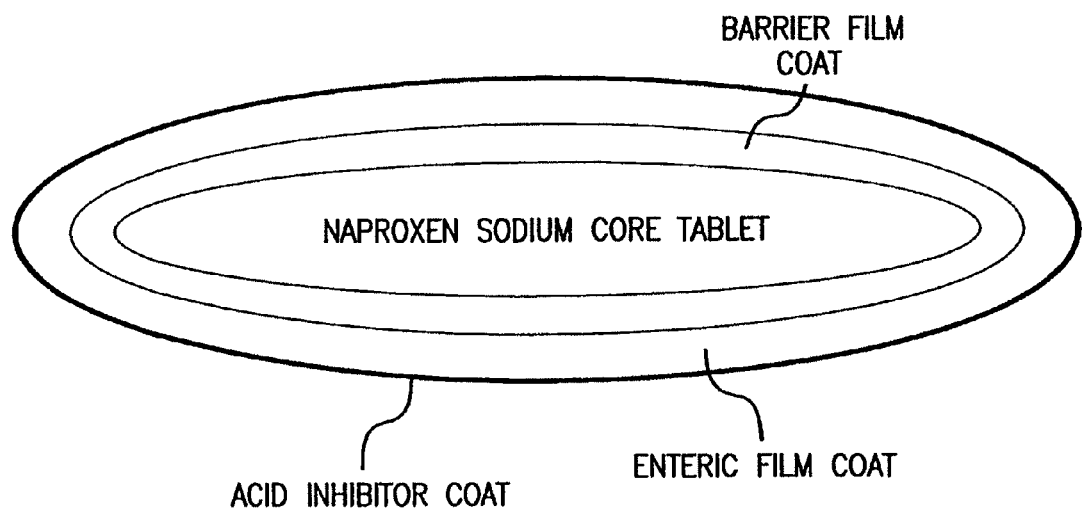
FIG. 1 is a schematic diagram of a four layer tablet dosage form. There is a naproxen core layer surrounded by a barrier layer. A third, enteric coating, layer delays the release of naproxen sodium until the pH is at a specific level, e.g., above 4. Finally, there is an outer layer that releases an acid inhibitor such as famotidine.

The present invention is based upon the discovery of improved pharmaceutical compositions for administering NSAIDs to patients. In addition to containing one or more NSAIDs, the compositions include acid inhibitors that are capable of raising the pH of the GI tract of patients. All of the dosage forms are designed for oral delivery and provide for the coordinated release of therapeutic agents, i.e., for the sequential release of acid inhibitor followed by analgesic.

The NSAIDs used in preparations may be either short or long acting. As used herein, the term "long acting" refers to an NSAID having a pharmacokinetic half-life of at least 2 hours, preferably at least 4 hours and more preferably, at least 8-14 hours. In general, its duration of action will equal or exceed about 6-8 hours. Examples of long-acting NSAIDs are: flurbiprofen with a half-life of about 6 hours; ketoprofen with a half-life of about 2 to 4 hours; naproxen or naproxen sodium with half-lives of about 12 to 15 hours and about 12 to 13 hours respectively; oxaprozin with a half life of about 42 to 50 hours; etodolac with a half-life of about 7 hours; indomethacin with a half-life of about 4 to 6 hours; ketorolac with a half-life of up to about 8-9 hours, nabumetone with a half-life of about 22 to 30 hours; mefenamic acid with a half-life of up to about 4 hours; and piroxicam with a half-life of about 4 to 6 hours. If an NSAID does not naturally have a half-life sufficient to be long acting, it can, if desired, be made long acting by the way in which it is formulated. For example, NSAIDs such as acetaminophen and aspirin may be formulated in a manner to increase their half-life or duration of action. Methods for making appropriate formulations are well known in the art (see e.g. *Remington's Pharmaceutical Sciences*, 16$^{th}$ ed., A. Oslo editor, Easton, Pa. (1980)).

It is expected that a skilled pharmacologist may adjust the amount of drug in a pharmaceutical composition or administered to a patient based upon standard techniques well known in the art. Nevertheless, the following general guidelines are provided:

Indomethacin is particularly useful when contained in tablets or capsules in an amount from about 25 to 75 mg. A typical daily oral dosage of indomethacin is three 25 mg doses taken at intervals during the day. However, daily dosages of up to about 150 mg are useful in some patients.

Aspirin will typically be present in tablets or capsules in an amount of between about 250 mg and 1000 mg. Typical daily dosages will be in an amount ranging from 500 mg to about 10 g. However, low dose aspirin present at 20-200 mg (and preferably 40-100 mg) per tablet or capsule may also be used.

Ibuprofen may be provided in tablets or capsules of 50, 100, 200, 300, 400, 600, or 800 mg. Daily doses should not exceed 3200 mg. 200 mg-800 mg may be particularly useful when given 3 or 4 times daily.

Flurbiprofen is useful when in tablets at about from 50 to 100 mg. Daily doses of about 100 to 500 mg, and particularly from about 200 to 300 mg, are usually effective.

Ketoprofen is useful when contained in tablets or capsules in an amount of about 25 to 75 mg. Daily doses of from 100 to 500 mg and particularly of about 100 to 300 mg are typical as is about 25 to 50 mg every six to eight hours.

Naproxen is particularly useful when contained in tablets or capsules in an amount of from 250 to 500 mg. For naproxen sodium, tablets of about 275 or about 550 mg are typically used. Initial doses of from 100 to 1250 mg, and particularly 350 to 800 mg are also used, with doses of about 550 mg being generally preferred.

Oxaprozin may be used in tablets or capsules in the range of roughly 200 mg to 1200 mg, with about 600 mg being preferred. Daily doses of 1200 mg have been found to be particularly useful and daily doses should not exceed 1800 mg or 26 mg/kg.

Etodolac is useful when provided in capsules of 200 mg to 300 mg or in tablets of about 400 mg. Useful doses for acute pain are 200-400 mg every six-eight hours, not to exceed 1200 mg/day. Patients weighing less than 60 kg are advised not to exceed doses of 20 mg/kg. Doses for other uses are also limited to 1200 mg/day in divided doses, particularly 2, 3 or 4 times daily.

Ketorolac is usefully provided in tablets of 1-50 mg, with about 10 mg being typical. Oral doses of up to 40 mg, and particularly 10-30 mg/day have been useful in the alleviation of pain.

Nabumetone may be provided in tablets or capsules of between 500 mg and 750 mg. Daily doses of 1500-2000 mg, after an initial dose of 100 mg, are of particular use.

Mefenamic acid is particularly useful when contained in tablets or capsules of 50 mg to 500 mg, with 250 mg being typical. For acute pain, an initial dosage of 1-1000 mg, and particularly about 500 mg, is useful, although other doses may be required for certain patients.

Lornoxicam is provided in tablets of 4 mg or 8 mg. Useful doses for acute pain are 8 mg or 16 mg daily, and for arthritis are 12 mg daily.

Other NSAIDs that may be used include: celecoxib, rofecoxib, meloxicam, piroxicam, droxicam, tenoxicam, valdecoxib, parecoxib, etoricoxib, CS-502, JTE-522, L-145,337, or NS398. JTE-522, L-745,337 and NS398 as described, inter alia, in Wakatani, et al. (*Jpn. J. Pharmacol.* 78:365-371 (1998)) and Panara, et al. (*Br. J. Pharmacol.* 116:2429-2434 (1995)). The amount present in a tablet or administered to a patient will depend upon the particular NSAID being used. For example:

Celecoxib may be administered in a tablet or capsule containing from about 100 mg to about 500 mg or, preferably, from about 100 mg to about 200 mg.

Piroxicam may be used in tablets or capsules containing from about 10 to 20 mg.

Rofecoxib will typically be provided in tablets or capsules in an amount of 12.5, 25 or 50 mg. The recommended initial daily dosage for the management of acute pain is 50 mg.

Meloxicam is provided in tablets of 7.5 mg, with a recommended daily dose of 7.5 or 15 mg for the management of osteoarthritis.

Valdecoxib is provided in tablets of 10 or 20 mg, with a recommended daily dose of 10 mg for arthritis or 40 mg for dysmenorrhea.

With respect to acid inhibitors, tablets or capsules may contain anywhere from 1 mg to as much as 1 g. Typical amounts for H2 blockers are: cimetidine, 100 to 800 mg/unit dose; ranitidine, 50-300 mg/unit dose; famotidine, 5-100 mg/unit dose; ebrotidine 400-800 mg/unit dose; pabutidine 40 mg/unit dose; lafutidine 5-20 mg/unit dose; and nizatidine, 50-600 mg/unit dose. Proton pump inhibitors will typically be present at about 5 mg to 600 mg per unit dose. For example, the proton pump inhibitor omeprazole should be present in tablets or capsules in an amount from 5 to 50 mg, with about 10 or 20 mg being preferred. Other typical amounts are: esomeprazole, 5-100 mg, with about 40 mg being preferred; lansoprazole, 5-150 mg (preferably 5-50 mg), with about 7.5, 15 or 30 mg being most preferred; pantoprazole, 10-200 mg, with about 40 mg being preferred; and rabeprazole, 5-100 mg, with about 20 mg being preferred.

Making of Pharmaceutical Preparations

The pharmaceutical compositions of the invention include tablets, dragees, liquids and capsules and can be made in accordance with methods that are standard in the art (see, e.g., *Remington's Pharmaceutical Sciences*, 16$^{th}$ ed., A Oslo editor, Easton, Pa. (1980)). Drugs and drug combinations will typically be prepared in admixture with conventional excipients. Suitable carriers include, but are not limited to: water; salt solutions; alcohols; gum arabic; vegetable oils; benzyl alcohols; polyethylene glycols; gelatin; carbohydrates such as lactose, amylose or starch; magnesium stearate; talc; silicic acid; paraffin; perfume oil; fatty acid esters; hydroxymethylcellulose; polyvinyl pyrrolidone; etc. The pharmaceutical preparations can be sterilized and, if desired, mixed with auxiliary agents such as: lubricants, preservatives, disintegrants; stabilizers; wetting agents; emulsifiers; salts; buffers; coloring agents; flavoring agents; or aromatic substances.

Enteric coating layer(s) may be applied onto the core or onto the barrier layer of the core using standard coating techniques. The enteric coating materials may be dissolved or dispersed in organic or aqueous solvents and may include one or more of the following materials: methacrylic acid copolymers, shellac, hydroxypropylmethcellulose phthalate, polyvinyl acetate phthalate, hydroxypropylmethylcellulose trimellitate, carboxymethylethyl-cellulose, cellulose acetate phthalate or other suitable enteric coating polymer(s). The pH at which the enteric coat will dissolve can be controlled by the polymer or combination of polymers selected and/or ratio of pendant groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates or other plasticizers. Additives such as dispersants, colorants, anti-adhering and anti-foaming agents may also be included.

The Making of Tablet Dosage Forms

Preferably, the combination of an acid inhibitor and an NSAID will be in the form of a bi- or multi-layer tablet. In a bilayer configuration, one portion of the tablet contains the acid inhibitor in the required dose along with appropriate excipients, agents to aid dissolution, lubricants, fillers, etc. The second portion of the tablet will contain the NSAID, preferably naproxen, in the required dose along with other excipients, dissolution agents, lubricants, fillers, etc. In the most preferred embodiment, the NSAID layer is surrounded by a polymeric coating which does not dissolve at a pH of less than 4. The NSAID may be granulated by methods such as slugging, low- or high-shear granulation, wet granulation, or fluidized-bed granulation. Of these processes, slugging generally produces tablets of less hardness and greater friability. Low-shear granulation, high-shear granulation, wet granulation and fluidized-bed granulation generally produce harder, less friable tablets.

EXAMPLES

Example 1

Enteric Coated Naproxen Sodium Core and Famotidine Immediate Release

A schematic diagram of a four layer tablet dosage form is shown in FIG. 1. The first layer contains naproxen sodium distributed throughout a matrix of pharmaceutically acceptable fillers, excipients, binding agents, disintegrants, and lubricants.

The second layer is a barrier layer which protects the first layer containing naproxen sodium. The barrier film coat is applied by conventional pan coating technology and the weight of the barrier coat may vary from 1% to 3% of the core tablet weight. In particular embodiments, the core naproxen sodium tablet is coated with coating ingredients such as Opaspray® K-1-4210A or Opadry® YS-1-7006 (Colorcon, West Point, Pa.). Polymer film coating ingredients such as hydroxypropylmethylcellulose 2910 and polyethylene glycol 8000 in a coating suspension may also be used.

The function of the third layer is to prevent the release of naproxen sodium until the dosage form reaches an environment where the pH is above about 4 or 5. The enteric coating does not dissolve in areas of the GI tract where the pH may be below about 4 or 5 such as in an unprotected stomach. Methacrylic acid copolymers are used as the enteric coating ingredient, triethyl citrate and dibutyl phthalate are plasticizers, and ammonium hydroxide is used to adjust the pH of the dispersion. The coating dissolves only when the local pH is above, for example, 5.5 and, as a result, naproxen sodium is released.

The outermost layer contains an "acid inhibitor" in an effective amount which is released from the dosage form immediately after administration to the patient. The acid inhibitor in the present example is a proton pump inhibitor or, preferably the H2 blocker famotidine, which raises the pH of the gastrointestinal tract to above 4. The typical effective amount of famotidine in the dosage form will vary from 5 mg to 100 mg. A typical film coating formulation contains Opadry Clear® YS-1-7006 which helps in the formation of the film and in uniformly distributing famotidine within the fourth layer without tablets sticking to the coating pan or to each other during application of the film coat. Other ingredients may include: plasticizers such as triethyl citrate, dibutyl phthalate, and polyethylene glycol; anti-adhering agents such as talc; lubricating ingredients such as magnesium stearate; and opacifiers such as titanium dioxide. In addition, the pH of the film coating solution can be adjusted to aid in dissolution of the famotidine. The film coating is thin and rapidly releases famotidine for absorption.

| Core Tablet Ingredients | % W/W | mg/Tablet |
| --- | --- | --- |
| Naproxen sodium, USP | 74.074 | 500.00 |
| Microcrystalline cellulose, NF (Avicel PH 200) | 17.166 | 115.87 |
| Povidone (K29/32), USP | 3.450 | 23.29 |
| Talc, USP | 4.350 | 29.36 |
| Magnesium Stearate, NF | 0.960 | 6.48 |
| Total | 100.00 | 675.00 |

| Barrier Film Coating Ingredients | % W/W |
| --- | --- |
| Opadry Clear ® YS-1-7006 | 5.00 |
| Purified water USP | 95.00 |
| Total | 100.00 |

| Enteric Coating Dispersion Ingredients | % W/W |
| --- | --- |
| Methacrylic Acid Copolymer, NF (Eudragit L-100-55) | 7.30 |
| Methacrylic Acid Copolymer, NF (Eudragit L-100) | 7.30 |
| Triethyl Citrate, NF | 2.95 |
| Dibutyl Phthalate, NF | 1.17 |
| Ammonium Hydroxide (30%), NF | 0.87 |
| Purified water, USP | 80.41 |
| Total | 100.00 |

| Famotidine Coating Dispersion Ingredients | % W/W |
| --- | --- |
| Famotidine, USP | 3.0 |
| Opadry Clear ® (YS-1-7006) | 5.0 |
| Talc, USP | 3.0 |
| Purified Water, USP | 89.0 |
| Total | 100.0 |

Example 2

Enteric Coated Naproxen Core and Famotidine Immediate Release

Figure 2:
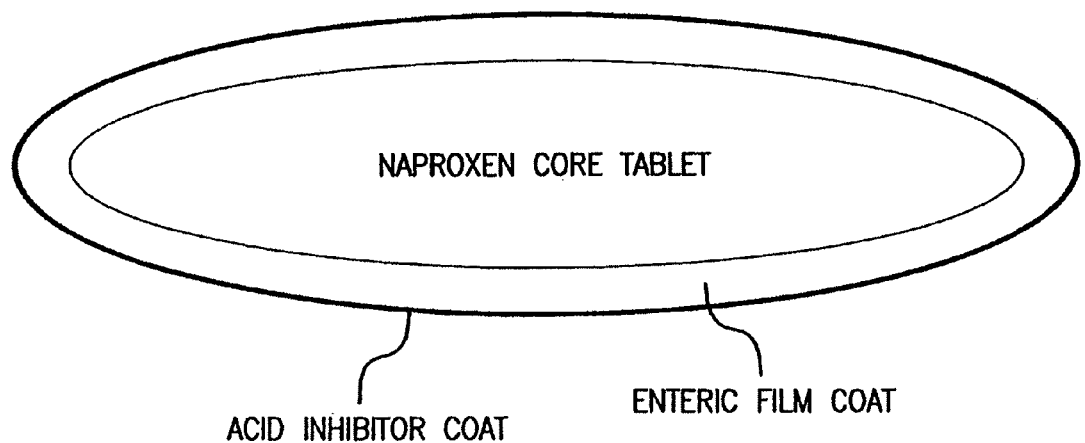
FIG. 2 illustrates a three layer dosage form. An acid inhibitor, e.g., famotidine, is released immediately after ingestion by a patient in order to raise the pH of the gastrointestinal tract to above a specific pH, e.g., above 4. The innermost layer contains naproxen. Thus, the dosage form has a naproxen core, an enteric film coat and an acid inhibitor film coat.

FIG. 2 illustrates a three layered dosage form which releases famotidine immediately after ingestion by the patient in order to raise the pH of the gastrointestinal tract to above about 4. The innermost layer contains naproxen uniformly distributed throughout a matrix of pharmaceutically acceptable excipients. These excipients perform specific functions and may serve as binders, disintegrants, or lubricants. A pharmaceutically acceptable enteric coating surrounds the naproxen core. The function of the enteric coat is to delay the release of naproxen until the dosage form reaches an environment where the pH is above about 4. The coating does not dissolve in the harshly acidic pH of the unprotected stomach. It contains methacrylic acid copolymers which prevent the release of naproxen in the unprotected stomach. Also included are: triethyl citrate, a plasticizer; simethicone emulsion, an anti-foaming agent; and sodium hydroxide which is used to adjust the pH of the dispersion.

The outermost layer contains an "acid inhibitor" in an effective amount which is released from the dosage form immediately after administration to the patient. The acid inhibitor in this example is a proton pump inhibitor or, preferably, the H2 blocker famotidine which raises the pH of the stomach to above 4. A typical film coating formulation contains Opadry Clear® YS-1-7006 which helps in the formation of the film and in uniformly distributing famotidine in the fourth layer without tablets sticking to the coating pan or sticking to each other during application of the film coat. Other ingredients are: plasticizers such as polyethylene glycol 8000; anti-adhering agents such as talc; lubricating ingredients such as magnesium stearate; and opacifiers such as titanium dioxide. In addition, the pH of the film coating solution can be adjusted to aid in dissolution of the famotidine. The film coating is thin and rapidly releases famotidine for absorption.

| Core Tablet Ingredients | % W/W | mg/Tablet |
|---|---|---|
| Naproxen, USP | 90.91 | 500.00 |
| Povidone K-90, USP | 2.00 | 11.00 |
| Starch, USP | 2.59 | 14.25 |
| Croscarmellose Sodium, USP | 4.00 | 22.00 |
| Magnesium Stearate, NF | 0.50 | 2.75 |
| Total | 100.00 | 550.00 |
| Purified Water, USP qs | | |

| Enteric Coating Dispersion Ingredients | % W/W |
|---|---|
| Methacrylic Acid Copolymer Type C, NF (Eudragit L-100-55) | 14.5 |
| Talc, USP | 3.8 |
| Sodium Hydroxide, NF | 0.2 |
| Triethyl Citrate, NF | 1.7 |
| Simethicone Emulsion, USP | 0.02 |
| Purified Water, USP | 79.78 |
| Total | 100.00 |

| Famotidine Coating Dispersion Ingredients | % W/W |
|---|---|
| Famotidine, USP | 3.0 |
| Opadry Clear ® (YS-1-7006) | 5.0 |
| Talc, USP | 3.0 |
| Purified Water, USP | 89.0 |
| Total | 100.0 |

Example 3

Naproxen Controlled Release Core and Famotidine Immediate Release

A trilayer tablet which separates famotidine contained in the film coat from controlled-release naproxen may be used in the present invention. The core tablet of naproxen is formulated using excipients which control the drug release for therapeutic relief from pain and inflammation for 24 hours. FIG. 2 shows an example of an appropriate trilayer tablet. In this particular example, naproxen is mixed with a polymeric material, hydroxypropyl-methylcellulose and granulated with water. The granules are dried, milled, and blended with a lubricant, such as magnesium stearate. They are then compacted into tablets.

The controlled-release core tablet of naproxen is film coated with a pharmaceutically acceptable enteric coating. The function of the enteric coat is to delay the release of naproxen until the dosage form reaches an environment where the pH is above about 4. The coating does not dissolve in the extremely acidic pH of the unprotected stomach. The function of methacrylic acid copolymers is to prevent the release of naproxen until the pH of the stomach rises. Triethyl citrate is a plasticizer, simethicone emulsion is a anti-foaming agent, and sodium hydroxide is used to adjust the pH of the dispersion.

The outermost layer contains an "acid inhibitor" which is released from the dosage form immediately after administration to the patient. The acid inhibitor in the present example is a proton pump inhibitor or, preferably, the H2 blocker famotidine which consistently raises the pH of the stomach to above 4. The typical effective amount of famotidine in the dosage will vary from 5 mg to 100 mg. A typical film coating formulation contains Opadry Blue® YS-1-4215 which is essential for film formation and for the uniform application of famotidine to the core tablet. Polymer film coating ingredients, hydroxypropylmethylcellulose or Opaspray® K-1-4210A (Colorcon, West Point, Pa.) may also be used. Other ingredients which help in the formation of the film and in the uniform application of famotidine to the core tablet are: plasticizers such as triethyl citrate and dibutyl phthalate; anti-adhering agents such as talc; lubricating ingredients such as magnesium stearate; and opacifiers such as titanium dioxide. In addition, the pH of the film coating solution can be adjusted to aid in dissolution of the famotidine. The film coating is thin and rapidly releases famotidine for absorption.

| Core Tablet Ingredients | % W/W | mg/Tablet |
|---|---|---|
| Naproxen, USP | 94.00 | 750 |
| Hydroxypropyl methylcellulose 2208, USP (viscosity 15000 cps) | 5.00 | 39.9 |
| Magnesium Stearate, NF | 1.00 | 7.95 |
| Total | 100.00 | 797.85 |

| Enteric Coating Dispersion Ingredients | % W/W |
|---|---|
| Methacrylic Acid Copolymer Type C, NF (Eudragit L-100-55) | 14.5 |
| Talc, USP | 3.8 |
| Sodium Hydroxide, NF | 0.2 |
| Triethyl Citrate, NF | 1.7 |
| Simethicone Emulsion, USP | 0.02 |
| Purified Water, USP | 79.78 |
| Total | 100.00 |

| Famotidine Coating Dispersion Ingredients | % W/W |
|---|---|
| Famotidine, USP | 2.0 |
| Opadry Blue ® (YS-1-4215) | 10.0 |
| Talc, USP | 9.0 |
| Purified Water, USP | 79.0 |
| Total | 100.0 |

Example 4

Naproxen and Famotidine Controlled Release Core and Famotidine Immediate Release A trilayer tablet which separates famotidine contained in the film coat from controlled-release naproxen and famotidine may be used in the present invention. The core tablet of naproxen and famotidine is formulated using excipients which control the drug release for therapeutic relief from pain and inflammation for 24 hours. FIG. 2 is an example of an appropriate trilayer tablet. In this particular example, naproxen and famotidine are mixed with a polymeric material, hydroxypropylmethylcellulose and granulated with water. The granules are dried, milled, and blended with a lubricant, such as magnesium stearate. They are then compacted into tablets.

The controlled-release core tablet of naproxen and famotidine is film coated with a pharmaceutically acceptable enteric coating. The function of the enteric coat is to delay the release of naproxen until the dosage form reaches an environment where the pH is above about 4. The coating does not dissolve in the extremely acidic pH of the unprotected stomach. The function of methacrylic acid copolymers is to prevent the release of naproxen until the pH of the stomach rises. Triethyl citrate is a plasticizer, simethicone emulsion is a anti-foaming agent, and sodium hydroxide is used to adjust the pH of the dispersion The outermost later contains an "acid inhibitor" which is released from the dosage form immediately after administration to the patient. The acid inhibitor in the present example is a proton pump inhibitor or, preferably, the H2 blocker famotidine which consistently raises the pH of the stomach to above 4. The typical effective amount of famotidine in the dosage will vary from 5 mg to 100 mg. A typical film coating formulation contains Opadry Blue® YS-1-4215 which is essential for film formation and for the uniform application of famotidine to the core tablet. Polymer film coating ingredients, hydroxypropylmethylcellulose or Opaspray® K-1-4210A (Colorcon, West Point, Pa.) may also be used. Other ingredients which help in the formation of the film and in the uniform application of famotidine to the core tablet are: plasticizers such as triethyl citrate and dibutyl phthalate; anti-adhering agents such as talc; lubricating ingredients such as magnesium stearate; and opacifiers such as titanium dioxide. In addition, the pH of the film coating solution can be adjusted to aid in dissolution of the famotidine. The film coating is thin and rapidly releases famotidine for absorption.

| Core Tablet Ingredients | % W/W | mg/Tablet |
| --- | --- | --- |
| Naproxen, USP | 88.05 | 500 |
| Famotidine, USP | 3.52 | 20.0 |
| Hydroxypropyl methylcellulose 2208, USP (viscosity 15000 cps) | 7.03 | 39.9 |
| Magnesium Stearate, NF | 1.40 | 7.95 |
| Total | 100.00 | 567.85 |

| Enteric Coating Dispersion Ingredients | % W/W |
| --- | --- |
| Methacrylic Acid Copolymer Type C, NF (Eudragit L-100-55) | 14.5 |
| Talc, USP | 3.8 |
| Sodium Hydroxide, NF | 0.2 |
| Triethyl Citrate, NF | 1.7 |
| Simethicone Emulsion, USP | 0.02 |
| Purified Water, USP | 79.78 |
| Total | 100.00 |

| Famotidine Coating Dispersion Ingredients | % W/W |
| --- | --- |
| Famotidine, USP | 2.0 |
| Opadry Blue ® (YS-1-4215) | 10.0 |
| Talc, USP | 9.0 |
| Purified Water, USP | 79.0 |
| Total | 100.0 |

Example 5

Enteric Coated Naproxen Sodium Core and Pantoprazole Immediate Release in Film Coat A schematic diagram of a four layer tablet dosage form is shown in FIG. 1. The first layer contains naproxen sodium distributed throughout a matrix of pharmaceutically acceptable fillers, excipients, binding agents, disintegrants, and lubricants.

The second layer is a barrier layer which protects the first layer containing naproxen sodium. The barrier film coat is applied by conventional pan coating technology and the weight of the barrier coat may vary from 1% to 3% of the core tablet weight. In particular embodiments, the core naproxen sodium tablet is coated with coating ingredients such as Opaspray® K-1-4210A or Opadry® YS-1-7006 (Colorcon, West Point, Pa.). Polymer film coating ingredients such as hydroxypropylmethylcellulose 2910 and polyethylene glycol 8000 in a coating suspension may also be used.

The third layer is an enteric film coat. It does not dissolve in areas of the GI tract where the pH may be below 4 such as in an unprotected stomach but it dissolves only when the local pH is above about 4. Therefore, the function of the third layer is to prevent the release of naproxen sodium until the dosage form reaches an environment where the pH is above 4. In this example, hydroxypropylmethylcellulose phthalate is the enteric coating ingredient, cetyl alcohol is a plasticizer and acetone and alcohol are solvents.

The fourth layer contains an "acid inhibitor" in an effective amount which is released from the dosage form as soon as the film coat dissolves. The acid inhibitor in this example is a proton pump inhibitor, pantoprazole, which raises the pH of the gastrointestinal tract to above 4. The typical effective amount of pantoprazole in the dosage form may vary from 10 mg to 200 mg. The film coat is applied by conventional pan coating technology and the weight of film coat may vary from 4% to 8% of the core tablet weight. Other ingredients are, plasticizers such as triethyl citrate, dibutyl phthalate, anti-adhering agents such as talc, lubricating ingredients such as magnesium stearate, opacifiers such as, titanium dioxide, and ammonium hydroxide to adjust the pH of the dispersion. The film coating is thin and rapidly releases pantoprazole for absorption. Therefore, pantoprazole releases first and then the core erodes and releases naproxen sodium.

| Core Tablet Ingredients | % W/W | mg/tablet |
|---|---|---|
| Naproxen sodium, USP | 74.075 | 500.00 |
| Microcrystalline cellulose, NF (Avicel PH 200) | 17.165 | 115.87 |
| Povidone (K29/32), USP | 3.450 | 23.29 |
| Talc, USP | 4.350 | 29.36 |
| Magnesium Stearate, NF | 0.960 | 6.48 |
| Total | 100.00 | 675.00 |

Naproxen sodium, 50% microcrystalline cellulose and povidone are dry mixed and wet granulated in an appropriate granulator with sufficient purified water. The wet granules are dried, milled, and blended with the remaining 50% microcrystalline cellulose, talc and magnesium stearate. The final granule blend is compressed into tablets.

| Barrier Film Coating Ingredients | % W/W |
|---|---|
| Opadry ® Clear YS-1-7006 | 5.00 |
| Purified Water, USP | 95.00 |
| Total | 100.00 |

Opadry clear is added slowly to purified water and mixing is continued until Opadry is fully dispersed. The solution is sprayed on to the tablet cores in a conventional coating pan until proper amount of Opadry clear is deposited on the tablets.

| Enteric Coating Ingredients | % W/W |
|---|---|
| Hydroxypropyl methylcellulose phthalate, NF | 5.5 |
| Cetyl alcohol, NF | 0.3 |
| Acetone, NF | 66.3 |
| Alcohol, USP | 27.9 |
| Total | 100.00 |

Hydroxypropylmethylcellulose phthalate and cetyl alcohol are dissolved in a mixture of alcohol and acetone. The solution is then sprayed on to the tablet bed in proper coating equipment. A sample of the tablets is tested for gastric resistance and the coating stopped if the tablets pass the test.

| Pantoprazole Film Coating Ingredients | % W/W |
|---|---|
| Pantoprazole sodium, USP | 5.00 |
| Opadry ® Clear YS-1-7006 | 5.00 |
| Sodium carbonate, NF | 1.20 |
| Purified Water, USP | 88.80 |
| Total | 100.00 |

Pantoprazole sodium is dissolved in purified water containing sodium carbonate in solution. After thorough mixing, Opadry clear is added slowly and mixing is continued until Opadry is fully dispersed. The suspension is sprayed on to the tablet cores in a conventional coating pan until the proper amount of pantoprazole sodium is deposited.

Example 6

Enteric Coated Naproxen Sodium Core and Omeprazole Immediate Release in Film Coat A schematic diagram of a four layer tablet dosage form is shown in FIG. 1. The first layer contains naproxen sodium distributed throughout a matrix of pharmaceutically acceptable fillers, excipients, binding agents, disintegrants, and lubricants.

The second layer is a barrier layer which protects the first layer containing naproxen sodium. The barrier film coat is applied by conventional pan coating technology and the weight of the barrier coat may vary from 1% to 3% of the core tablet weight. In particular embodiments, the core naproxen sodium tablet is coated with coating ingredients such as Opaspray® K-1-4210A or Opadry® YS-1-7006 (Colorcon, West Point, Pa.). Polymer film coating ingredients such as hydroxypropylmethylcellulose 2910 and polyethylene glycol 8000 in a coating suspension may also be used.

The third layer is an enteric film coat. It does not dissolve in areas of the GI tract where the pH is below 4 such as in an unprotected stomach but it dissolves only when the local pH is above 4. Therefore, the function of the third layer is to prevent the release of naproxen sodium until the dosage form reaches an environment where the pH is above about 4. In this example, hydroxypropylmethylcellulose phthalate is the enteric coating ingredient, cetyl alcohol is a plasticizer and acetone and alcohol are solvents.

The fourth layer contains an "acid inhibitor" in an effective amount which is released from the dosage form as soon as the film coat dissolves. The acid inhibitor in this example is a proton pump inhibitor, omeprazole, which raises the pH of the gastrointestinal tract to above 4. The typical effective amount of omeprazole in the dosage form may vary from 5 mg to 50 mg. The film coat is applied by conventional pan coating technology and the weight of film coat may vary from 4% to 8% of the core tablet weight. Other ingredients are, plasticizers such as triethyl citrate, dibutyl phthalate, anti-adhering agents such as talc, lubricating ingredients such as magnesium stearate, opacifiers such as, titanium dioxide, and ammonium hydroxide to adjust the pH of the dispersion. The film coating is thin and rapidly releases omeprazole for absorption. Therefore, omeprazole is released first and then the core erodes and releases naproxen sodium.

| Core Tablet Ingredients | % W/W | mg/tablet |
|---|---|---|
| Naproxen sodium, USP | 74.075 | 500.00 |
| Microcrystalline cellulose, NF (Avicel PH 200) | 17.165 | 115.87 |
| Povidone (K29/32), USP | 3.450 | 23.29 |
| Talc, USP | 4.350 | 29.36 |
| Magnesium Stearate, NF | 0.960 | 6.48 |
| Total | 100.00 | 675.00 |

Naproxen sodium, 50% microcrystalline cellulose and povidone are dry mixed and wet granulated in an appropriate granulator with sufficient purified water. The wet granules are dried, milled, and blended with the remaining 50% microcrystalline cellulose, talc and magnesium stearate. The final granule blend is compressed into tablets.

| Barrier Film Coating Ingredients | % W/W |
|---|---|
| Opadry ® Clear YS-1-7006 | 5.00 |
| Purified Water, USP | 95.00 |
| Total | 100.00 |

Opadry clear is added slowly to purified water and mixing is continued until Opadry is fully dispersed. The solution is sprayed on to the tablet cores in a conventional coating pan until the proper amount of Opadry clear is deposited on the tablets.

| Enteric Coating Ingredients | % W/W |
|---|---|
| Methacrylic Acid Copolymer, NF (Eudragit L-100-55) | 6.0 |
| Triethyl Citrate, NF | 0.6 |
| Talc, USP | 3.0 |
| Purified Water, USP | 5.0 |
| Isopropyl Alcohol, USP | 85.40 |
| Total | 100.00 |

Methacrylic acid copolymer, triethyl citrate, and talc are dissolved in a mixture of isopropyl alcohol and water. The solution is then sprayed on to the tablet bed in a proper coating equipment. A sample of the tablets is tested for gastric resistance and the coating is stopped if the tablets pass the test.

| Omeprazole Film Coating Ingredients | % W/W |
|---|---|
| Omeprazole, USP | 5.00 |
| Opadry ® Clear YS-1-7006 | 5.00 |
| Purified Water, USP | 10.00 |
| Isopropyl Alcohol, USP | 80.00 |
| Total | 100.00 |

Omeprazole is dissolved in a purified water and isopropyl alcohol mixture. After thorough mixing, Opadry clear is added slowly and mixing is continued until Opadry is fully dispersed. The suspension is sprayed on to the tablet cores in a conventional coating pan until proper amount of omeprazole is deposited on the tablets.

Example 7

Naproxen Sodium Delayed Release and Omeprazole Immediate Release Capsule

A coordinated delivery dosage may be used to provide fast release of an acid inhibitor, a proton pump inhibitor, omeprazole which raises the pH of the gastrointestinal tract to above 4, and the delayed release of a non-steroidal anti-inflammatory drug, naproxen sodium. Omeprazole granules modify the pH of the stomach such that the drug readily dissolves and is absorbed in the stomach without significant degradation. The typical effective amount of omeprazole in the dosage form may vary from 5 mg to 50 mg. The release of naproxen sodium is delayed by enteric coating.

Omeprazole granules contain an alkalizing excipient such as sodium bicarbonate. Other soluble alkalizing agents such as potassium bicarbonate, sodium carbonate, sodium hydroxide, or their combinations may also be used. The alkalizing agent helps solubilize and protect omeprazole from degradation before its absorption. Sodium lauryl sulfate helps in the wetting of omeprazole. Other surfactants may be used to perform the same function. In the present example, hydroxypropyl methylcellulose helps in granule formation, sodium starch glycolate is a disintegrant, and magnesium stearate is a lubricant. Other excipients may also be used to perform these functions.

Figure 3:
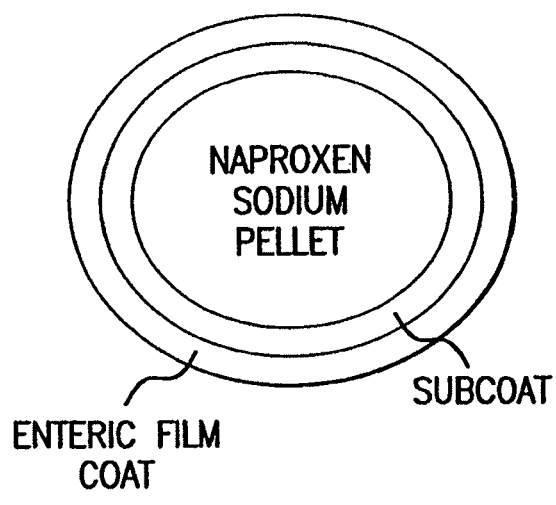
FIG. 3 illustrates a naproxen sodium pellet which contains a subcoat or barrier coat prior to the enteric film coat.

Naproxen sodium pellets as shown in FIG. 3 are prepared by the wet massing technique and the conventional extrusion and spheronization process. The excipients used in the formulation are microcrystalline cellulose, and povidone. The pellets after drying and classification are coated with a protective subcoating containing povidone. Other coating ingredients may also be used such as Opaspray K-1-4210A or Opadry YS-1-7006 (trademarks of Colorcon, West Point, Pa.). Polymer film coating ingredients such as hydroxypropylmethylcellulose 2910 and polyethylene glycol 8000 in a subcoating suspension are also alternatives. Other ingredients are, plasticizers such as triethyl citrate, dibutyl phthalate, anti-adhering agents such as talc, lubricating ingredients such as magnesium stearate, opacifiers such as, titanium dioxide.

The subcoated pellets are enteric coated using enteric coating polymers. In this example, the enteric coating polymer is methacrylic acid copolymer and the plasticizer is dibutyl phthalate which are dissolved in a mixture of acetone and alcohol. The enteric film does not dissolve in the acidic pH but dissolves when the pH in the gut is above about pH 6 and releases naproxen sodium.

| mmmOmeprazole Granules | % W/W | mg/capsule |
|---|---|---|
| Omeprazole, USP | 12.9 | 20.00 |
| Sodium Bicarbonate, USP | 82.40 | 127.72 |
| Hydroxypropyl methylcellulose, USP | 2.00 | 3.10 |
| Sodium lauryl sulfate, NF | 0.20 | 0.31 |
| Sodium starch glycolate, NF | 2.00 | 3.10 |
| Magnesium stearate, NF | 0.50 | 0.77 |
| Total | 100 | 100 |

Hydroxypropylmethylcellulose is dissolved in water, then sodium lauryl sulfate is added and the solution is mixed. Omeprazole, microcrystalline cellulose, and sodium bicarbonate are dry mixed together and granulated with the granulating solution. The granulation is mixed until proper granule formation is reached. The granulation is then dried, milled, and blended with magnesium stearate.

| Pellet Ingredients | % W/W | mg/tablet |
|---|---|---|
| Naproxen sodium, USP | 86.80 | 250.00 |
| Microcrystalline cellulose, NF (Avicel PH 200) | 11.10 | 32.00 |
| Povidone (K90), USP | 2.10 | 6.00 |
| Total | 100.00 | 288.00 |

Povidone is dissolved in water. Naproxen sodium and microcrystalline cellulose are dry mixed and granulated with povidone solution. The wet mass is mixed until proper consistency is reached. The wet mass is then pressed through an extruder and spheronized to form pellets. The pellets are then dried and classified into suitable particle size range.

| Subcoat Ingredients | % W/W |
|---|---|
| Povidone (K29-32), USP | 10.00 |
| Alcohol, USP | 90.00 |
| Total | 100.00 |

The pellet cores are coated using povidone solution by a conventional coating pan method to a weight gain of 1-2%.

| Enteric Coating Ingredients | % W/W |
|---|---|
| Methacrylic Acid Copolymer, NF (Eudragit L-100) | 8.20 |
| Diethyl Phthalate, NF | 1.70 |
| Acetone, NF | 33.30 |
| Isopropyl Alcohol, USP | 56.80 |
| Total | 100.0 |

Eudragit L-100 is dissolved in isopropanol and acetone and diethyl phthalate is dissolved. The solution is sprayed on the pellet cores using proper film coating equipment. A sample of the pellets is tested for gastric resistance before stopping the coating process.

Omeprazole fast release granules and naproxen sodium delayed release pellets are blended together and filled into appropriate size capsules to contain 250 mg naproxen sodium and 20 mg omeprazole per capsule.

Example 8

Naproxen Delayed Release and Omeprazole Immediate Release Capsule

The present Example is directed to a coordinated delivery dosage form containing omeprazole and naproxen. The formulation contains 10 mg omeprazole and uses methylcellulose as a binder and croscarmellose sodium as a disintegrant. Naproxen pellets as shown in FIG. 3 do not need a subcoating layer and are enteric coated with an aqueous dispersion of methacrylic acid copolymer. Optionally, these pellets could be compressed into a core and film coated with an acid inhibitor and thereby form a bilayer tablet.

| Omeprazole Granules | % W/W | mg/capsule |
|---|---|---|
| Omeprazole, USP | 6.45 | 10.00 |
| Sodium Bicarbonate, USP | 88.85 | 137.71 |
| Methylcellulose, USP | 2.00 | 3.10 |
| Sodium lauryl sulfate, NF | 0.20 | 0.31 |
| Croscarmellose sodium, NF | 2.00 | 3.10 |
| Magnesium stearate, NF | 0.50 | 0.78 |
| Total | 100 | 100 |

Methylcellulose is dissolved in water, then sodium lauryl sulfate is added to the solution and mixed. Omeprazole, microcrystalline cellulose, and sodium bicarbonate are dry mixed together and granulated with the granulating solution. The granulation is mixed until proper granule formation is reached. The granulation is then dried, milled, and blended with magnesium stearate.

| Pellet Ingredients | % W/W | mg/tablet |
|---|---|---|
| Naproxen, USP | 76. | 250.00 |
| Microcrystalline cellulose, NF (Avicel PH 200) | 21. | 71.44 |
| Povidone (K90), USP | 2. | 6.56 |
| Total | 100. | 328.00 |

Povidone is dissolved in water. Naproxen and microcrystalline cellulose are dry mixed and granulated with povidone solution. The wet mass is mixed until proper consistency is reached. The wet mass is then pressed through an extruder and spheronized to form pellets. The pellets are then dried and classified into a suitable particle size range.

| Enteric Coating Ingredients | % W/W |
|---|---|
| Methacrylic Acid Copolymer, NF (Eudragit L30D 30% dispersion) | 15.60 |
| Talc, USP | 7.60 |
| Triethyl citrate, NF | 1.60 |
| Simethicone Emulsion, USP (Silicone antifoam emulsion SE 2) | 0.20 |
| Purified Water, USP | 74.80 |

Eudragit 30D is dispersed in purified water and simethicone emulsion. Talc and triethyl citrate are then dispersed. The suspension is sprayed on the pellet cores using proper film coating equipment. A sample of the pellets is tested for gastric resistance before stopping the coating process. Omeprazole fast release granules and naproxen sodium delayed release pellets are blended together and filled into appropriate size capsules to contain 250 mg naproxen and 10 mg omeprazole per capsule.

Example 9

Clinical Study of the Relationship of Gastric pH to NSAID-Induced Gastric Ulcers Sixty-two subjects were enrolled in a clinical study and randomly assigned to three groups. The following three groups were administered study medication twice daily for five days: (a) 550 mg naproxen sodium (n=10), (b) 40 mg famotidine given with 550 mg of naproxen or famotidine followed 90 minutes later by 550 mg naproxen, (n=39) or (c) 20 mg omeprazole followed by 550 mg naproxen sodium (n=13). Gastric pH was measured hourly beginning at the time of dosing of the final daily dose of study medication and for 8-10 hours thereafter. Subjects had a gastric endoscopy performed at the beginning and on Day 5 prior to the morning dose of study medication to identify gastric and duodenal irritation; no subjects were admitted to the study if gastric irritation was present at the time of initial endoscopy.

Five patients, three (33%) in the naproxen alone group and two (5%) in the famotidine/naproxen group, presented with gastroduodenal ulcers at the end of the study. In the naproxen alone group, the pH was greater than 4 only 4% of the time, and in the famotidine/naproxen group the pH was greater than 4 forty-nine percent of the time during the 8-10 hours following naproxen sodium dosing. Additionally, Lanza grade 3 or 4 damage was present in 28% (n=11) of the subjects receiving famotidine/naproxen sodium, and present 100% (n=10) in the naproxen sodium treatment group. Monitoring of gastric acidity on day 5 indicated that patients with Lanza scores of greater than 2 had integrated gastric acidity of greater than 100 mmol-hr./L. Only 20-40% of patients with integrated gastric acidity of less than 100 mmol-hr/L had gastric pathology, whereas all patients with integrated gastric acidity greater than 100 mmol-hr/L had pathology.

Example 10

Famotidine and Enteric Coated Naproxen Reduce Gastroduodenal Damage Due to NSAID Therapy Thirty-seven patients were randomized to two groups for a one week study of twice-daily dosing of: 500 mg enteric coated naproxen, and 500 mg enteric coated naproxen preceded by 40 mg famotidine. Endoscopies were conducted on all patients prior to first dosing and on the final day of the study. No subjects had evidence of gastroduodenal damage at the beginning of the study (at first endoscopy).

At the second endoscopy, Lanza scores for gastroduodenal damage were assessed for all subjects. 39% of the subjects in the enteric coated naproxen 500 mg group had grade 3-4 gastroduodenal damage. This is lower than the percentage that would be expected for the administration of 500 mg of non-enteric naproxen based upon previous work. Nevertheless, subjects administered 500 mg enteric coated naproxen and 40 mg famotidine had an even lower incidence of grade 3-4 gastroduodenal damage (26%) than subjects who had previously taken enteric coated naproxen alone which demonstrates the value of combining acid inhibition with enteric coating of NSAID to minimize the gastrointestinal damage.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A pharmaceutical composition in unit dosage form comprising therapeutically effective amounts of:
    (a) esomeprazole, wherein at least a portion of said esomeprazole is not surrounded by an enteric coating; and
    (b) naproxen surrounded by a coating that inhibits its release from said unit dosage form unless said dosage form is in a medium with a pH of 3.5 or higher wherein said coating comprises methacrylic acid copolymers;
    wherein said unit dosage form provides for release of said esomeprazole such that upon introduction of said unit dosage form into a medium, at least a portion of said esomeprazole is released regardless of the pH of the medium.

2. The pharmaceutical composition of claim 1, wherein naproxen is present in said unit dosage form in an amount of 200-600 mg.

3. The pharmaceutical composition of claim 1, wherein esomeprazole is present in said unit dosage form in an amount of from 5 to 100 mg.

4. The pharmaceutical composition of claim 1, wherein naproxen is present in said unit dosage form in an amount of between 200-600 mg and esomeprazole in an amount of from 5 to 100 mg per unit dosage form.

* * * * *